United States Patent
Kessler et al.

(10) Patent No.: US 8,780,354 B2
(45) Date of Patent: Jul. 15, 2014

(54) MARKER-FREE CHROMOSOME SCREENING

(75) Inventors: Rudolf Kessler, Reutlingen (DE); Tobias Merz, Thun (CH); Karsten Rebner, Leinfelden (DE)

(73) Assignee: Hochschule Reutlingen, Reutlingen (DE)

( * ) Notice: Subject to any disclaimer, the term of this patent is extended or adjusted under 35 U.S.C. 154(b) by 481 days.

(21) Appl. No.: 12/919,789

(22) PCT Filed: Feb. 19, 2009

(86) PCT No.: PCT/EP2009/051953
§ 371 (c)(1),
(2), (4) Date: Nov. 24, 2010

(87) PCT Pub. No.: WO2009/106473
PCT Pub. Date: Sep. 3, 2009

(65) Prior Publication Data
US 2011/0058177 A1    Mar. 10, 2011

(30) Foreign Application Priority Data

Feb. 27, 2008    (DE) .................... 10 2008 011 283

(51) Int. Cl.
G01J 3/45      (2006.01)
G01N 21/45     (2006.01)
G01N 21/31     (2006.01)

(52) U.S. Cl.
CPC .............. *G01N 21/45* (2013.01); *G01N 21/31* (2013.01)
USPC ......................................................... 356/451

(58) Field of Classification Search
CPC ............... G01N 21/45; C12Q 2565/60; C12Q 2565/601
USPC ........................................................... 356/451
See application file for complete search history.

(56) References Cited

U.S. PATENT DOCUMENTS

| | | | | |
|---|---|---|---|---|
| 6,165,734 | A | * | 12/2000 | Garini et al. ................. 435/7.21 |
| 6,194,148 | B1 | | 2/2001 | Hori |
| 8,445,217 | B2 | * | 5/2013 | Bornhop ........................ 435/7.2 |
| 2005/0244863 | A1 | | 11/2005 | Mir |
| 2009/0098534 | A1 | * | 4/2009 | Weier et al. ....................... 435/6 |
| 2009/0147264 | A1 | * | 6/2009 | Lotze ............................. 356/477 |

FOREIGN PATENT DOCUMENTS

| | | |
|---|---|---|
| DE | 200510042733 | 4/2006 |
| DE | 200610023887 | 11/2007 |
| WO | 9858288 | 12/1998 |

OTHER PUBLICATIONS

Bayani, et al., "Applications of SKY in cancer cytogenetics", Cancer Inv. J., 20 (3):373-86 (2002).
Betzig, et al., "Near-field optics: microscopy and surface modification beyond the diffraction limit", Science, 257(5067):189-95 (1992).

(Continued)

*Primary Examiner* — Jonathan Hansen
(74) *Attorney, Agent, or Firm* — Pabst Patent Group LLP

(57) ABSTRACT

The present invention relates to a method for analyzing chromosomes through preparing a chromosome preparation, measuring at least one interference characteristic of the chromosome preparation and characterizing at least one chromosome structure by way of the interference characteristic. Also, the invention relates to the use of a near-field microscope for analyzing un-dyed chromosomes.

15 Claims, 17 Drawing Sheets

(56) References Cited

OTHER PUBLICATIONS

Beuthan, et al., "The spatial resolution of near-field ooptical misroscope on chromosomes and cell traces", J. Selected Topics in Quasntum Elect., 7(6) (2001).

Caspersson, et al., "Chemical differentiation along metaphase chromosomes" Exp. Cell Res., 49:219-22 (1968).

Fujita, et al., "Label-free molecular imaging of living cells", Molecules and Cells, 26(6):530-35 (2008).

Ghislain, et al., "Near-field scanning solid immersion microscope", Appl. Physics Lttrs, 72(22):2779-81 (1998).

Hartmann, "An elementary introduction to atomic force microscopy and related methods", Internet citation http://www.uni-arland.de/fac7/hartmann/files/docs/pdf/download/IntroductionAfm.pdf>, 35-36 (2009).

Mansfield, et al., "Solid immersion microscope", Appl. Physics Lttrs., 57 (24):2615-16 (1990).

Merz, et al., "Spectroscopic imaging in the near field with an apertureless solid immersion lens microscope", Proceed. of thr Spie Intl. Soc. for Optical Eng., 6631:1-12 (2007).

Merz, et al., "Breaking the diffraction limit by near field micorscopeiwht a solid immersion lens AFM combination", Doktorandenseminar, 3:9-12 (2008).

Moers, et al., "Optical contrast in near-filed techniques", Ultramicroscopy, 57 (2-3):298-302 (1995).

Oberringer, et al., "Atomic force microsacopy and scanning near-field optical microscopy studies on the characterization of human metaphase chromosomes", Eu. Biophysics J., 32:620-27 (2003).

Van Hulst, et al., "Biological applications of near-field optical microscopy", IEEE Eng. In Med and Biol. Mag., 15(1):51-58 (1996).

Zhao, et al., "A simple efficient method of sequential G-banding and fluorescence in situhybridzation", Cancer Genet Cytogenet, 101:62-64 (1998).

ISR for EP2009051953 mailed Aug. 20, 2009.

Ofice Action mailed Apr. 29, 2009 (english Trans.).

\* cited by examiner

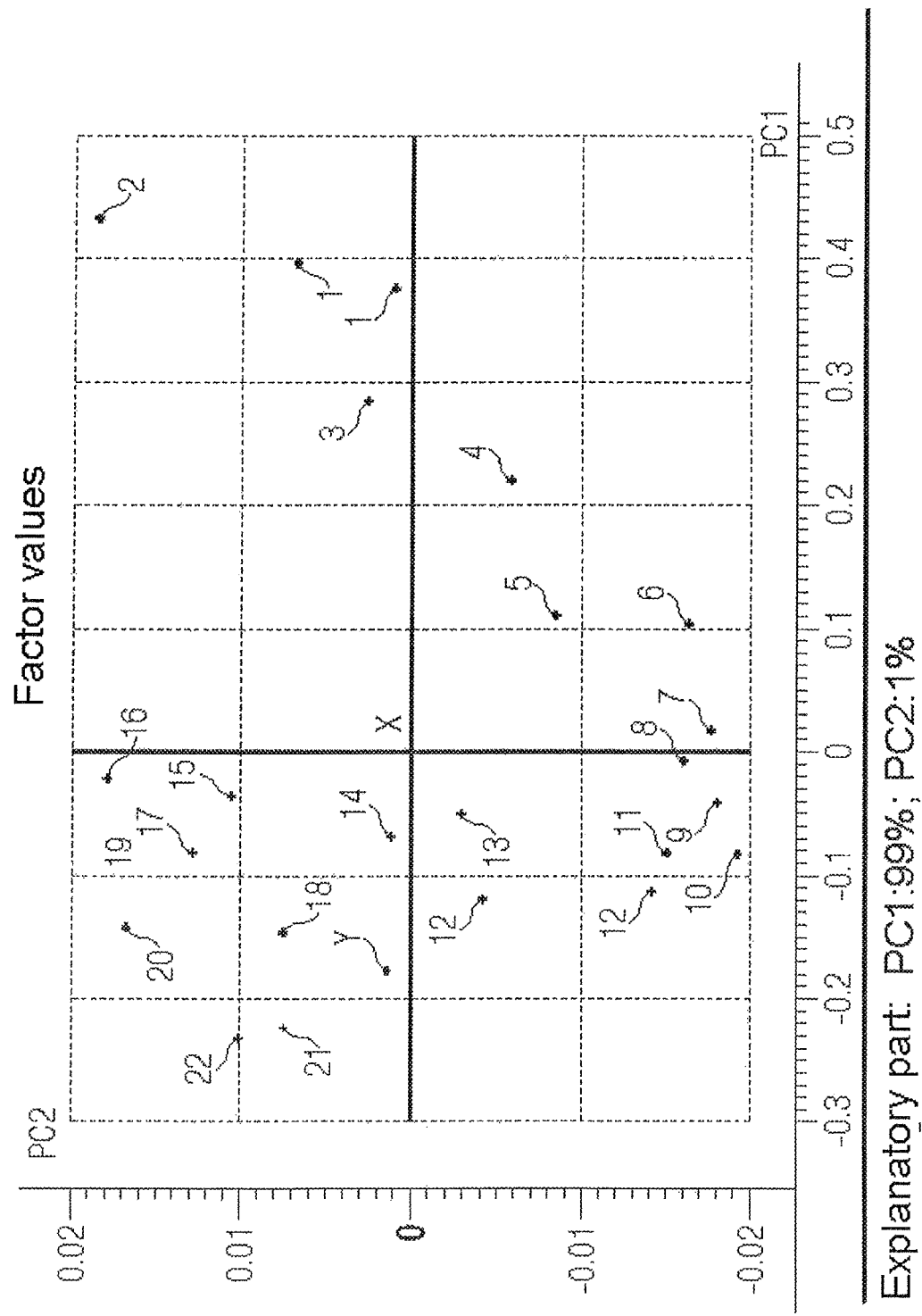

MARKER-FREE CHROMOSOME SCREENING

FIELD OF THE INVENTION

The invention relates to a method for analyzing chromosomes and to the use of a near field microscope for the analysis of unstained chromosomes.

BACKGROUND OF THE INVENTION

Chromosomes are structures, which contain genes and, thereby, hereditary information. They contain DNA which is packed with proteins and are to be found in the nuclei of eukaryotic cells.

In the middle of the 20th century techniques were developed in order to analyze the number and structure of cells which were metaphasing. In a metaphase preparation the chromosomes of a cell lie spread out beside one another, i.e. spread out on a microscope slide so that they can be counted under the microscope and compared with one another. In good preparations the individual chromosomes have the frequently displayed X-like shape.

A classic staining technique to display metaphase chromosomes is the Giesma staining. After the chromosomes have been treated with the enzyme trypsin the chromatin complex of DNA and bound histon proteins is stained with Methylene Blue. Depending upon the base composition, chromatin condensation and the time-point of the replication alternate dark-colored sections (G-bands) and light-colored sections (R-bands) are formed. The banded profile makes it possible to obtain an unambiguous identification of all the chromosomes in humans and some animals (Zhao et al., 1998).

Other analytical methods for chromosomes which are based upon staining techniques are fluorescence in situ hybridisation (FISH) and spectral karyotyping (SKY).

In the FISH technique artificially-produced probes of nucleic acids are employed which hybridize by base pairing to the nucleic acid to be detected. After hybridization, which takes from 1 hour to several days, hybrid molecules made from the nucleic acids of the preparation and the probe are present. The bound probe molecules can be detected. With an indirect marking, the detection is done using an antibody stain or Avidin which in turn are bound to fluorochromes. For each fluorochrome, individual pictures are taken using filter systems which are then superimposed (Bayani und Squire, 2002; Zhao et al., 1998).

The SKY technique is based upon Fourier Spectroscopy in which an interferometer allows the measurement of the entire emitted light spectrum for each pixel. To facilitate this, chromosome specific color probes are employed so that each chromosome receives a characteristic emission spectrum. By converting these specific spectra into pseudo colors it is possible to identify each chromosome and, if appropriate, chromosomal aberrations (Bayani und Squire, 2002).

In the analysis of stained chromosomes, the color quality, the degree of condensation and the spread determine the banded profile or the spectral properties of the chromosomes. In this way, the significance of these techniques for possible structural anomalies of the chromosomes varies depending upon the staining and preparation methods. A further disadvantage of the staining techniques is the time intensive nature of their execution and analysis which require special methodical skill and a precise knowledge of the banding of chromosomes. Furthermore repeated staining or double staining, such as, for example, FISH on Giemsa is often necessary to allow analysis to be carried out and verified.

In addition to the techniques based on staining described above, atomic force microscopy uses unmarked chromosomes. In this case karyotypization is carried out based on the length, width, height or volume or the specific height profile of each chromosome as a microscopically small needle scans over the surface of the sample. Technically this method is extremely demanding and highly sensitive to disturbance by vibration, heat and static loading. Furthermore it exhibits system generated faults so that rather than producing an image of the actual surface of the sample an image of the folding of the geometry of the needle point with the structure of the surface is produced.

With the help of chromosome analysis, variations in the karyotype, i.e. changes of the chromosome number, such as, for example trisomy 21, monosomy X, or structural aberrations such as, for example, translocation, deletion, inversion can be detected. In diagnostics a distinction is made between prenatal and postnatal chromosome analysis as well as pre-implantation analysis. By means of prenatal karyotyping it is possible to examine fetuses during pregnancy following an amniocentesis or a chorionic villus biopsy for possible diseases and damages. Particularly in the field of prenatal diagnostics there is a great need for a quick and reliable test for karyotyping which can also be carried out by non-specialist personnel working in a physician's practice. Because of the increasing age of expectant parents prenatal diagnostics have earned an increasing level of importance.

Until now, in the prior art a chromosome analysis is carried out solely by disturbance-prone, elaborate atomic force techniques or by staining techniques which are time consuming and depend upon staining quality, degree of condensation and spreading of the chromosomes. Furthermore, an analysis based upon staining techniques requires a precise knowledge of chromosome banding.

The present invention, therefore, faces the problem of providing a quick and simple method for improved chromosome analysis which is independent of marking or staining techniques.

According to the invention this problem is solved by a method for analyzing chromosomes. In the method according to the invention a chromosome preparation is made and its interference properties are measured, thereby characterizing chromosome structures.

SUMMARY OF THE INVENTION

The present invention relates to a method for analyzing chromosomes by
a) providing a chromosome preparation;
b) measuring at least one interference property of the chromosome preparation; and
c) characterizing at least one chromosome structure by means of the interference property.

Furthermore, the invention relates to the use of a near field microscope for the analysis of unstained chromosomes.

BRIEF DESCRIPTION OF THE FIGURES

The figures serve to explain the invention. It is not intended that they limit the invention to the concrete embodiments depicted.

B: Preparation on a Si-wafer, reflected light dark field (Reflection arrangement 45/0)
C: Preparation on gold, reflected light dark field (Reflection arrangement 45/0)
D: Preparation on gold, reflected light bright field (Reflection arrangement 0/0)

Figure 1:
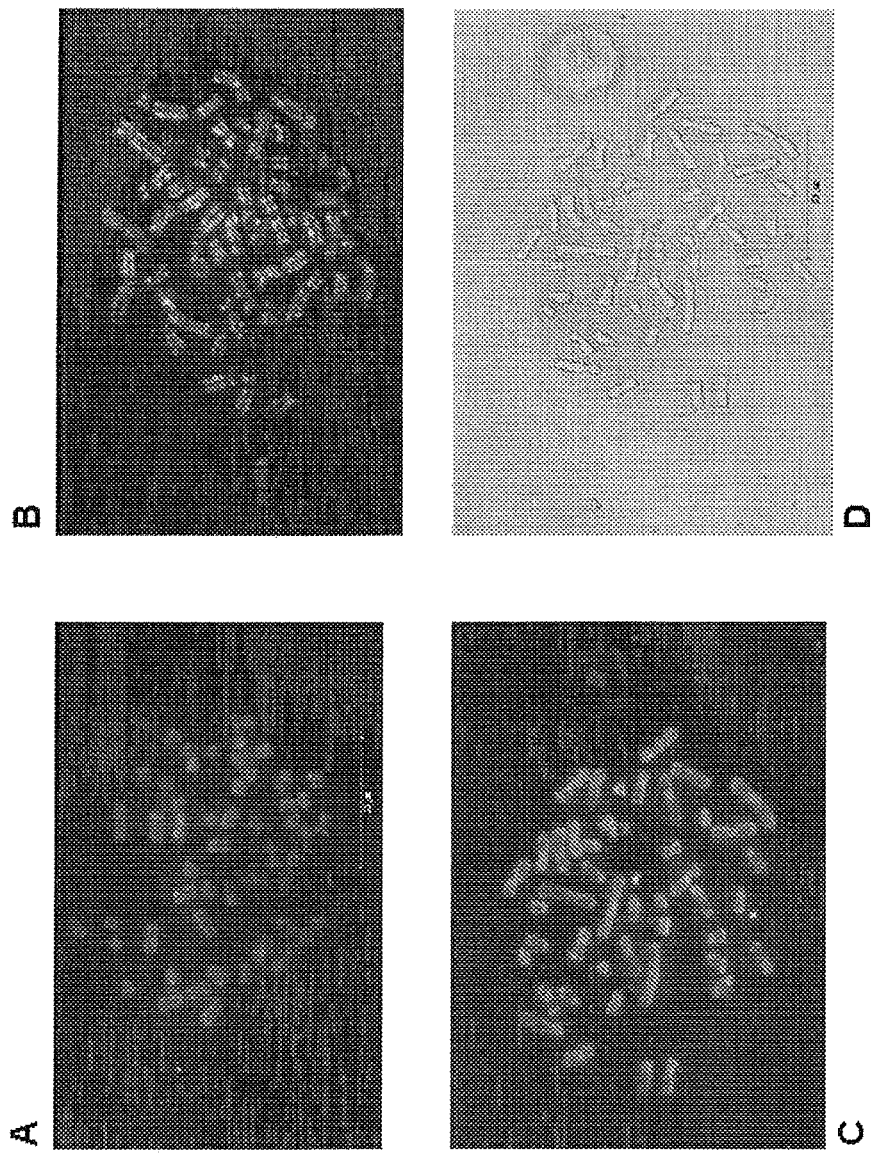
FIGS. 1A to 1D each illustrate an unstained set of chromosomes on different materials and subjected to different measurement arrangements
A: Preparation on glass, reflected light dark field (Reflection arrangement 45/0)
Figure 2:
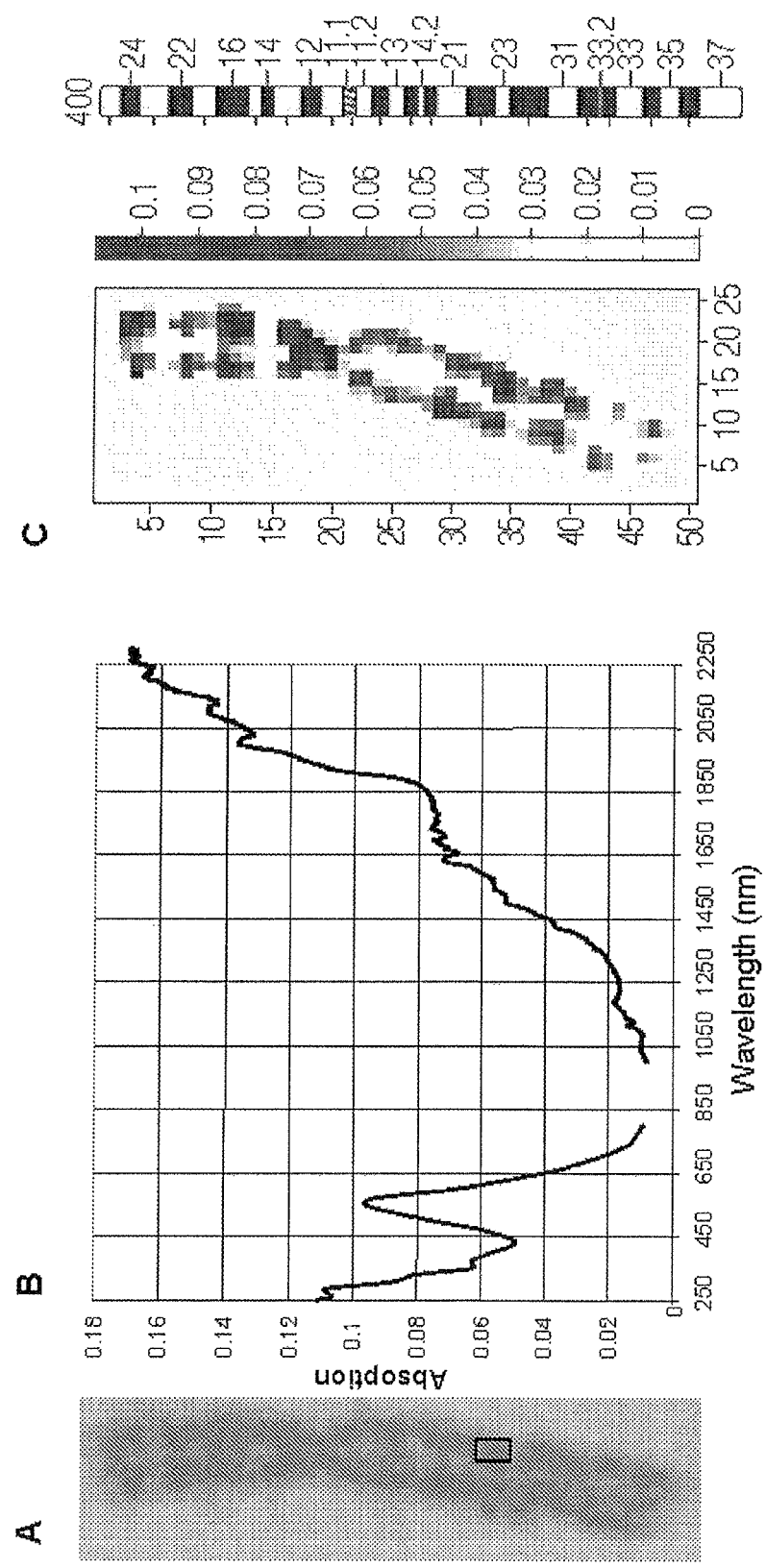

FIG. 2 shows a mapping of human chromosome No. 2 with Giemsa Trypsin Giemsa (GTG) banding in transmission.

Figure 3A:
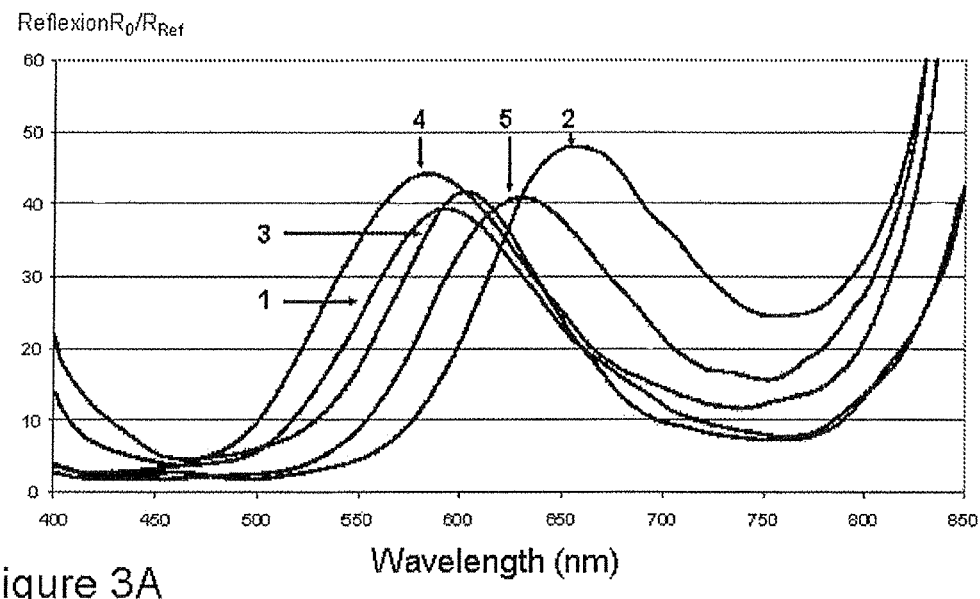
Figure 3B:
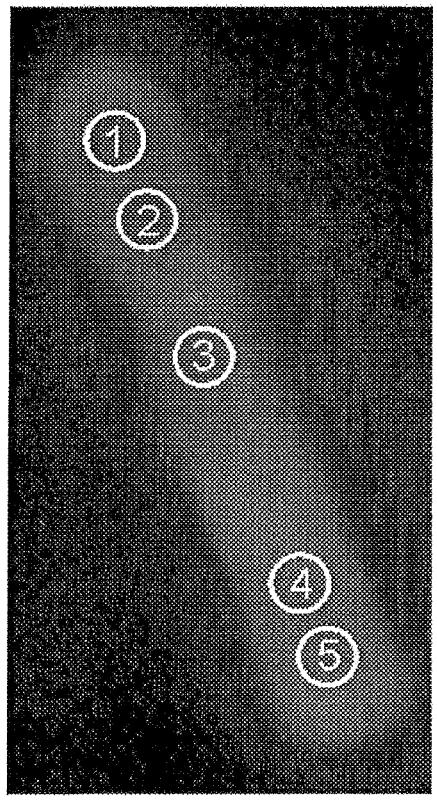

FIG. 3 shows individual reflection spectra of chromosome No. 2 from FIG. 3B, displayed in reflected light dark field.

Figure 4:
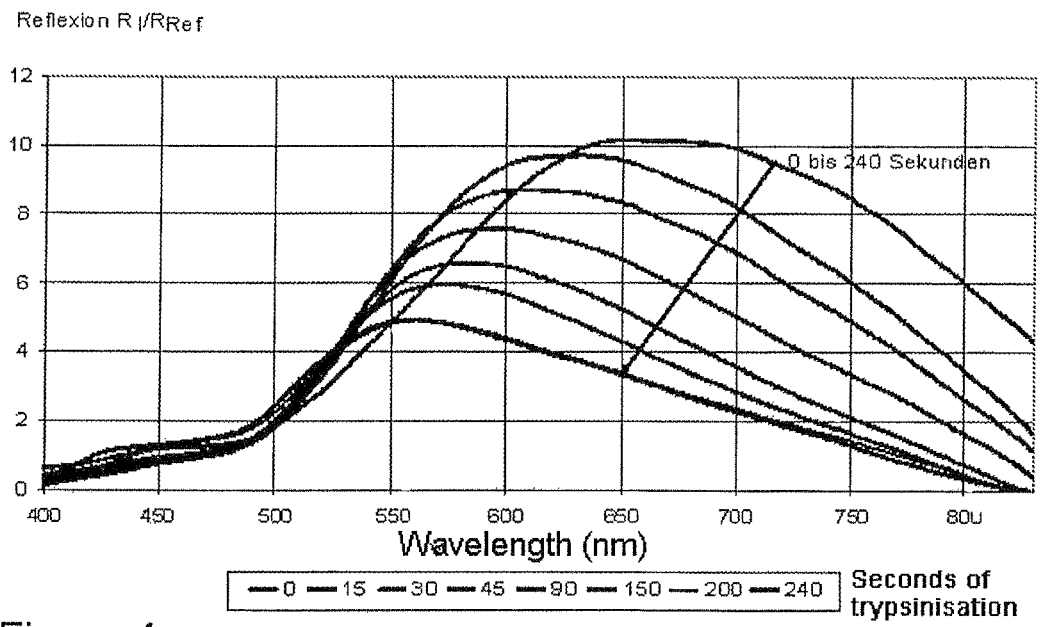

FIG. 4 shows a total spectrum of chromosome No. 2 displayed in reflected light dark field after different trypsin exposure times.

Figure 5:
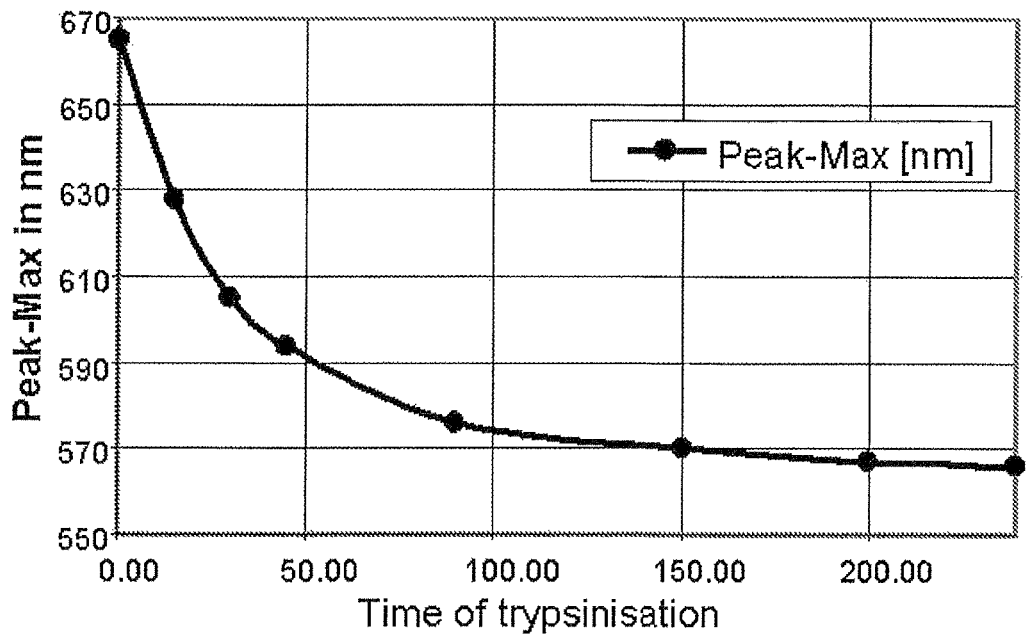

FIG. 5 shows a functional correlation between peak maximum and trypsin exposure time.

Figure 6A:
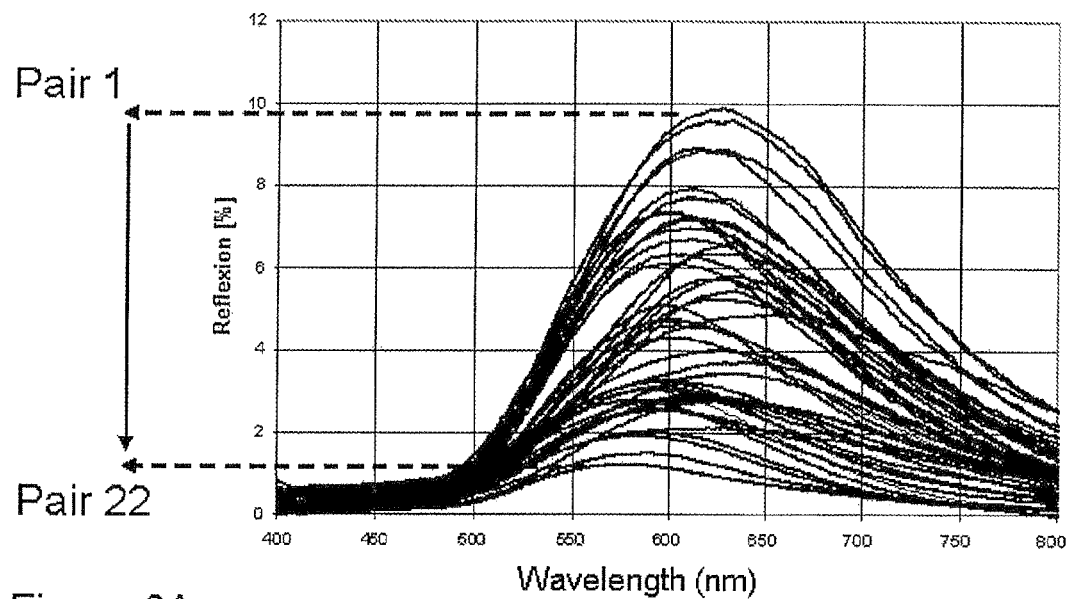
Figure 6B:
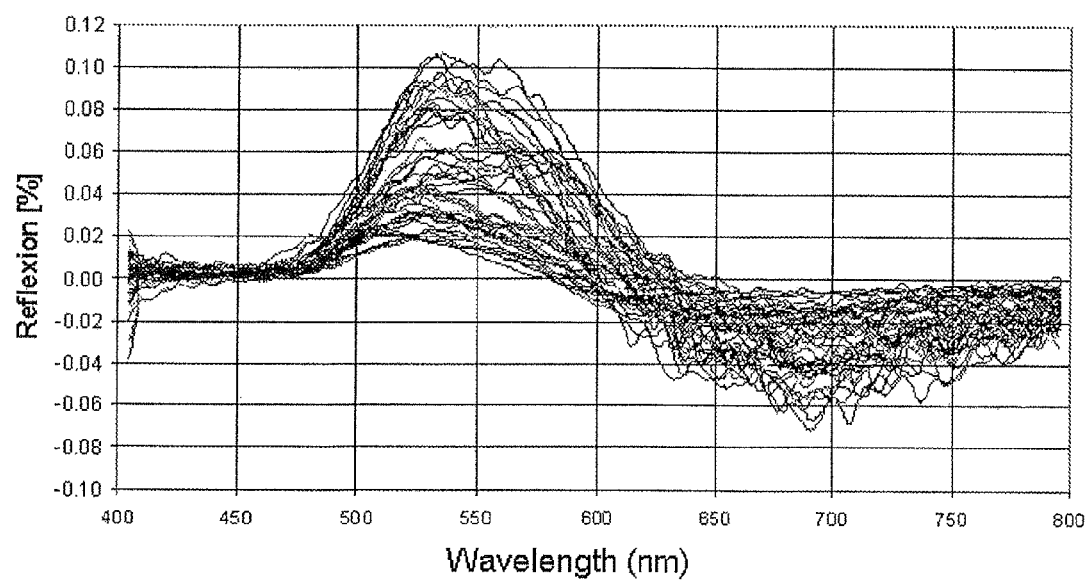

FIG. 6A shows 46 reflection spectra of the chromosomes. FIG. 6B shows the 1st derivation of the spectra.

FIG. 7 shows a principal component analysis of derived individual spectra.
A: The score matrix for principal components 1 and 2.
B: The factor diagrams for principal components 1 and 2.

Figure 8:
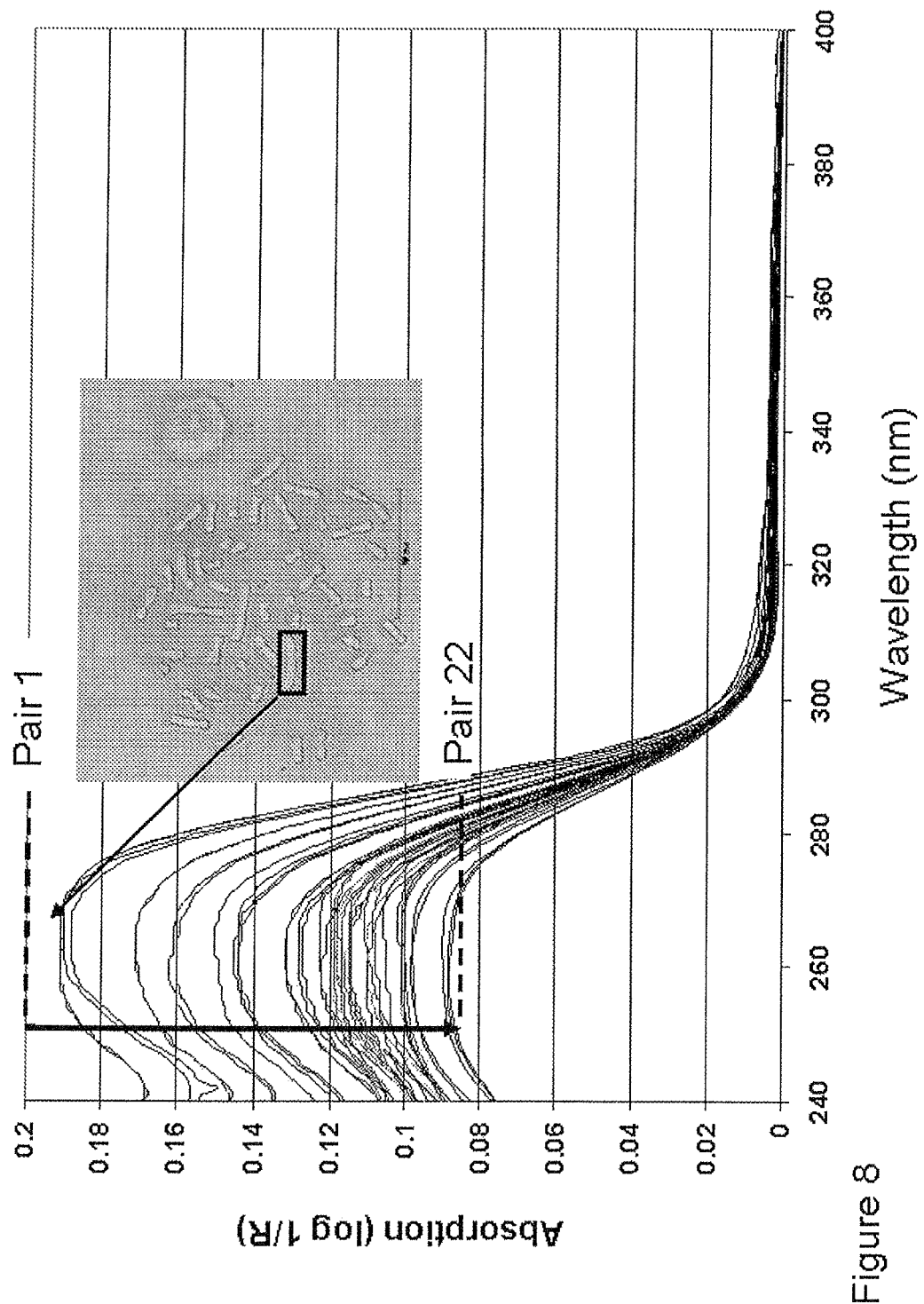

FIG. 8 shows ultraviolet (UV) reflection spectra of each chromosome; X-axis: wavelength, Y-axis: absorption.

FIG. 9 shows a principal component analysis of the individual spectra of UV reflection spectra.
A: The score matrix for principal components 1 and 2.
B: The factor diagrams for principal components 1 and 2.

Figure 10A:
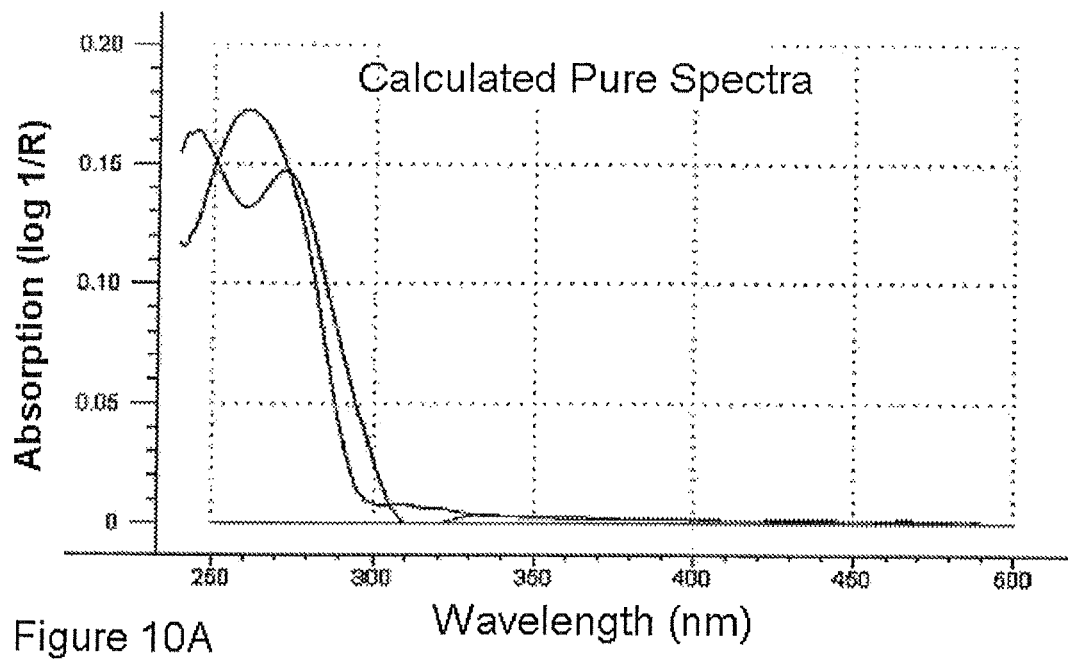
Figure 10B:
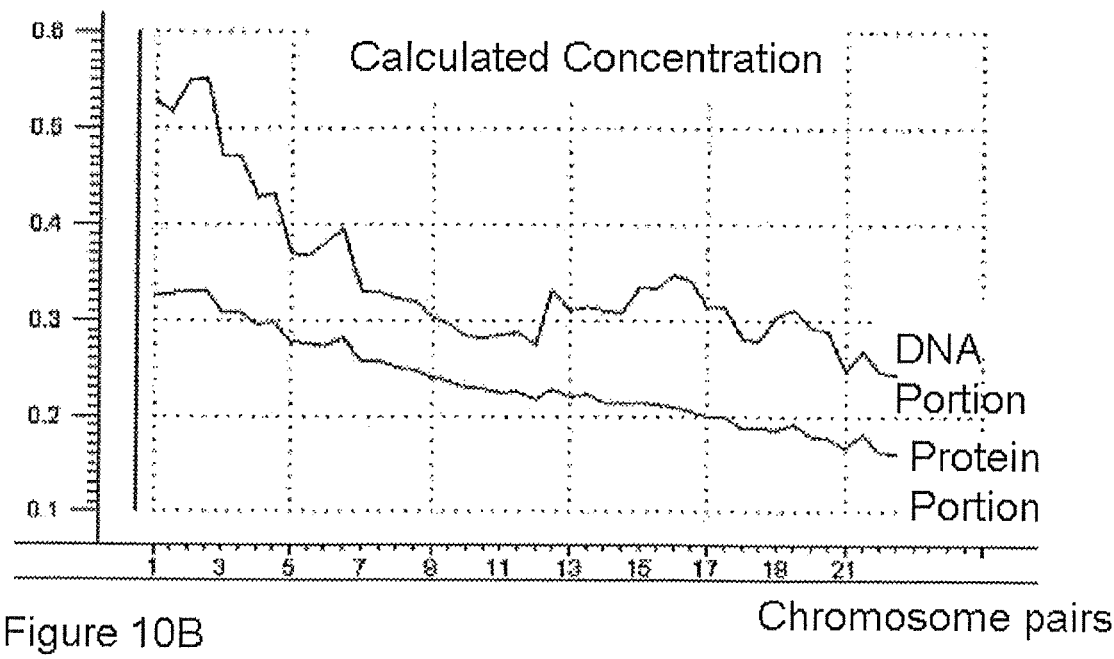

FIGS. 10A and 10B show a resolution of the multivariate curves (Multivariate Curve Resolution (MCR)) as an evaluation of the UV reflection spectra.

Figure 11:
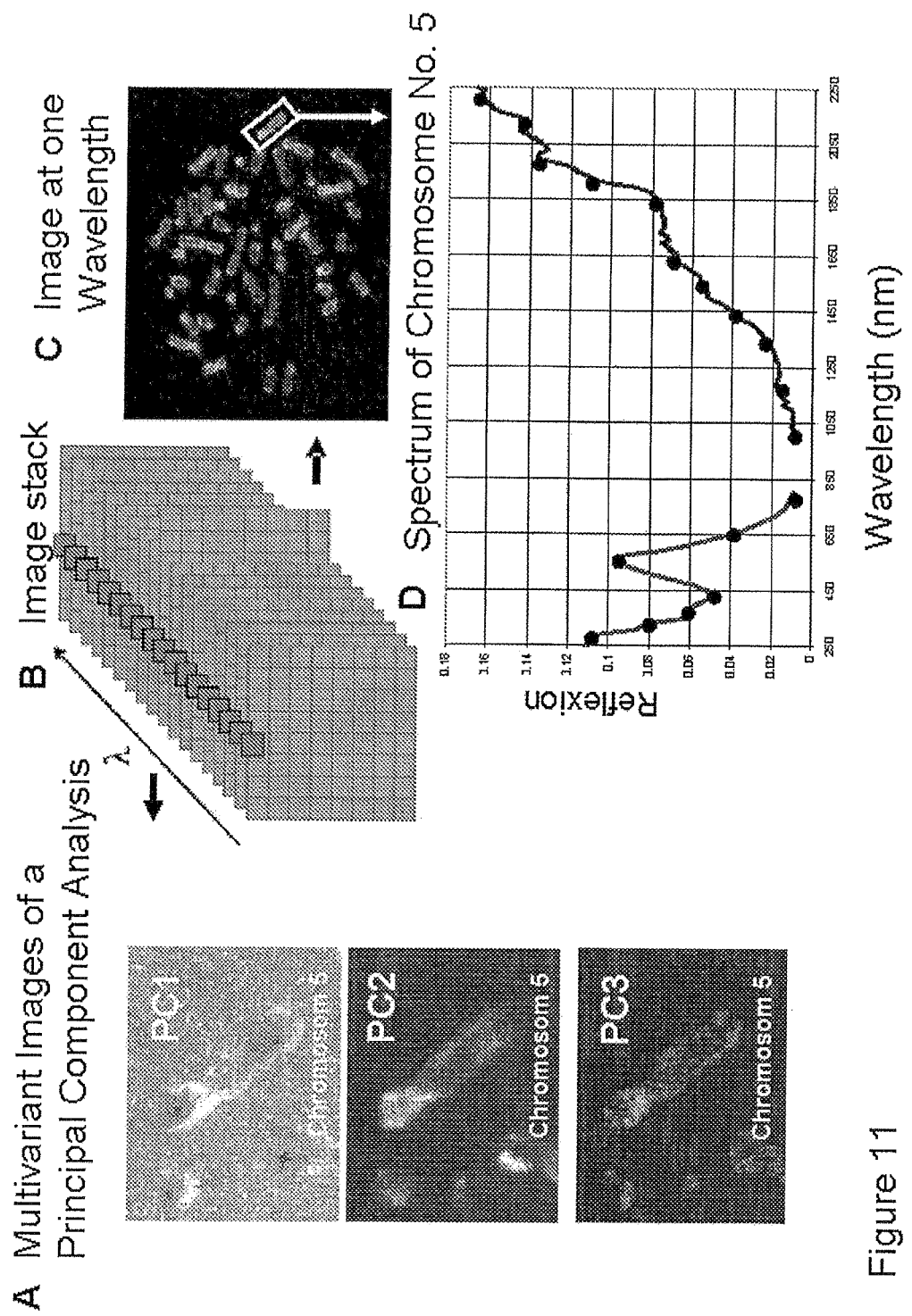

FIG. 11 shows a multivariate image analysis (MIA) of an unstained chromosome set in the form of a principal component analysis after 2D scanning with dependence upon wavelength.
A: Individual images of chromosome No. 5.
B: Image stack and diagram of the 2D scan.
C: Image of the unstained chromosome set at one wavelength.
D: Spectrum of chromosome No. 5.

Figure 12:
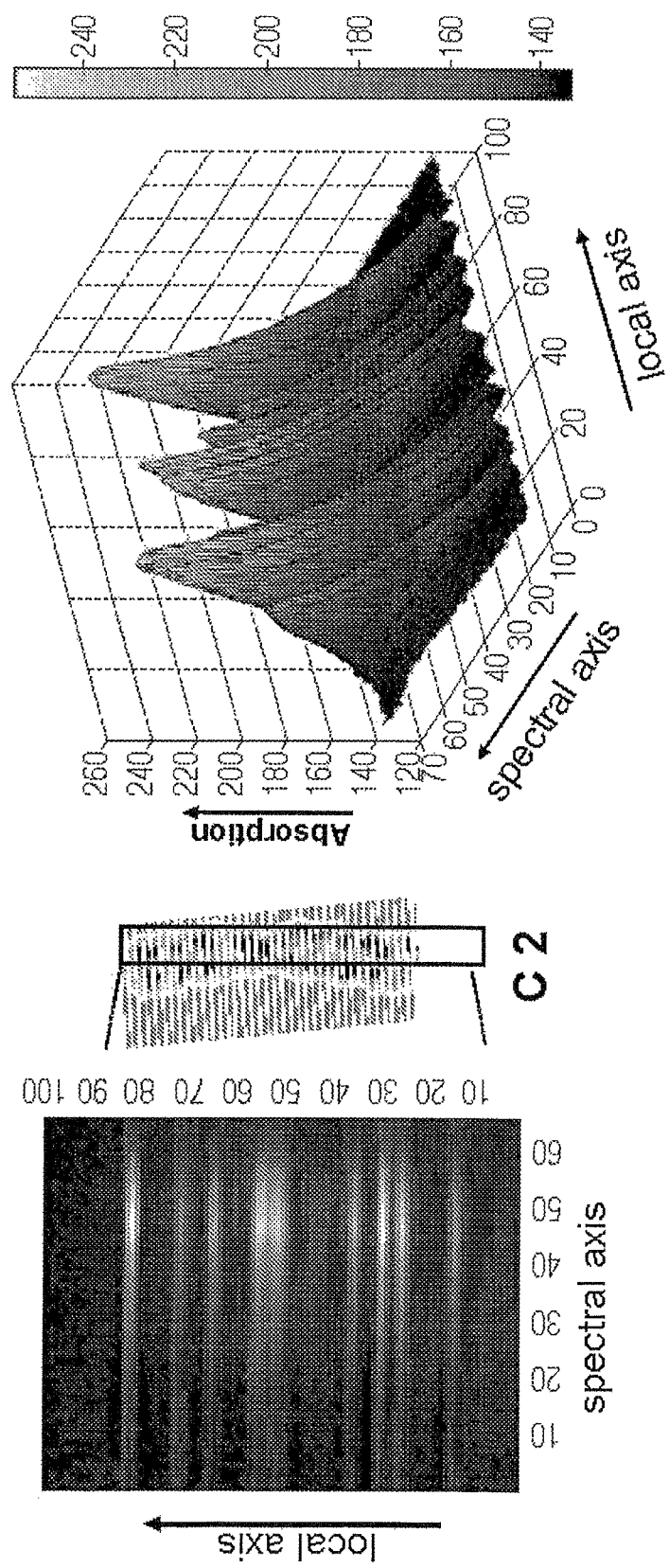

FIG. 12 shows a pushbroom representation of chromosome No. 2 after GTG banding in transmission.

Figure 13:
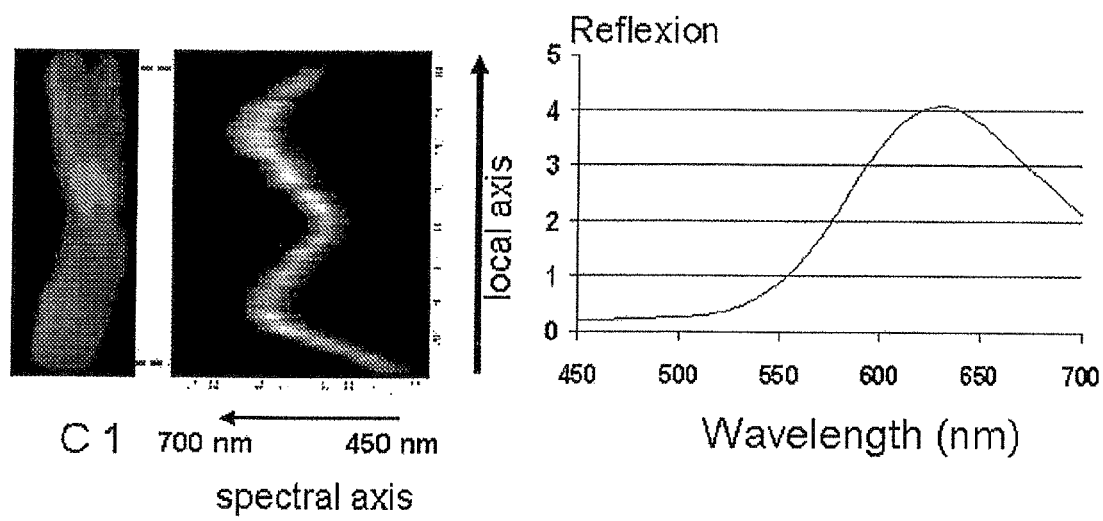

FIG. 13 shows a pushbroom representation in the visual (VIS) region.

Figure 14:
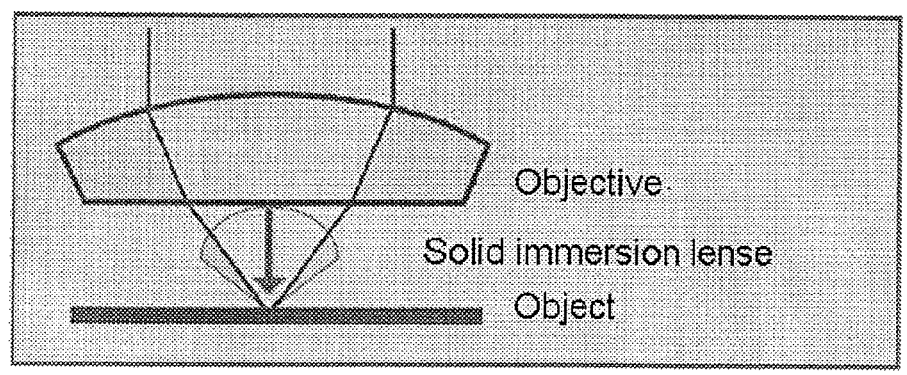

FIG. 14 shows the schematic arrangement of objective, solid immersion lens and object as they were used in the one embodiment of the invention.

Figure 15:
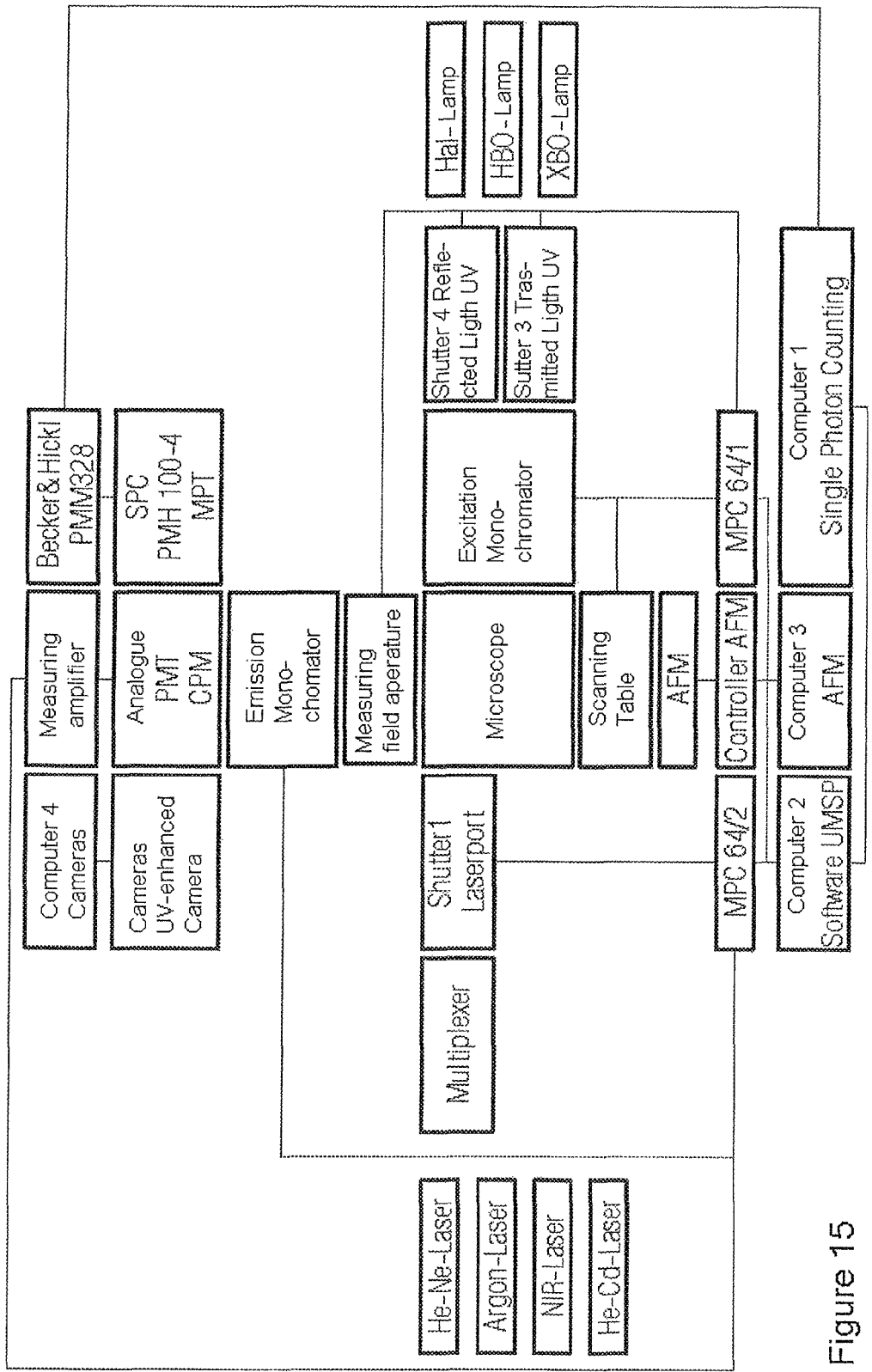

FIG. 15 shows the schematic arrangement of the apparatus used for near field microscopy and near field spectroscopy.

Figure 16:
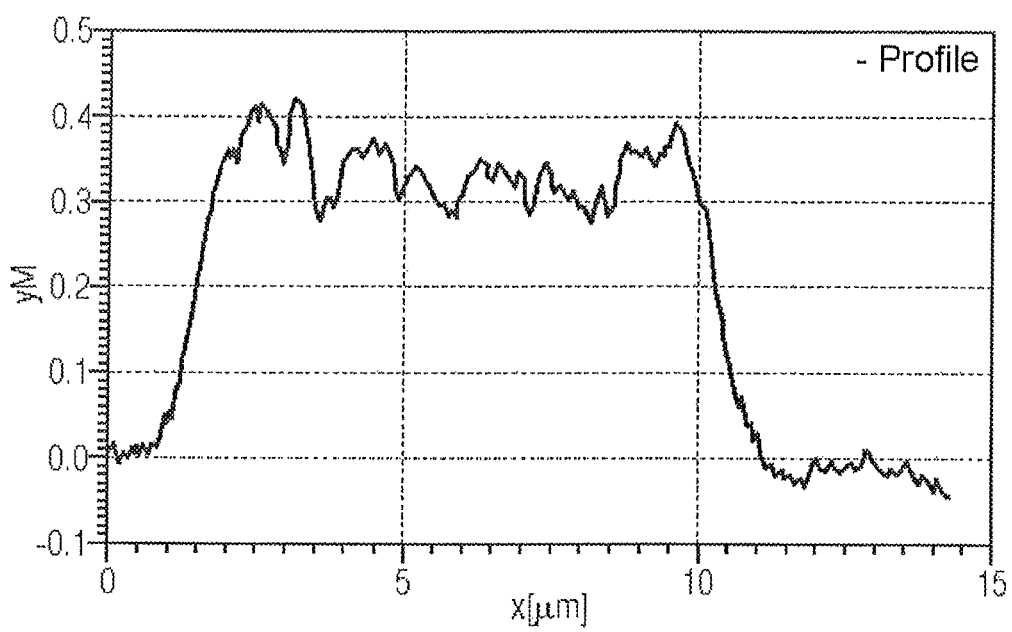

FIG. 16 shows an intensity profile of an unstained chromosome, which was recorded with a near field microscope.

Figure 17:
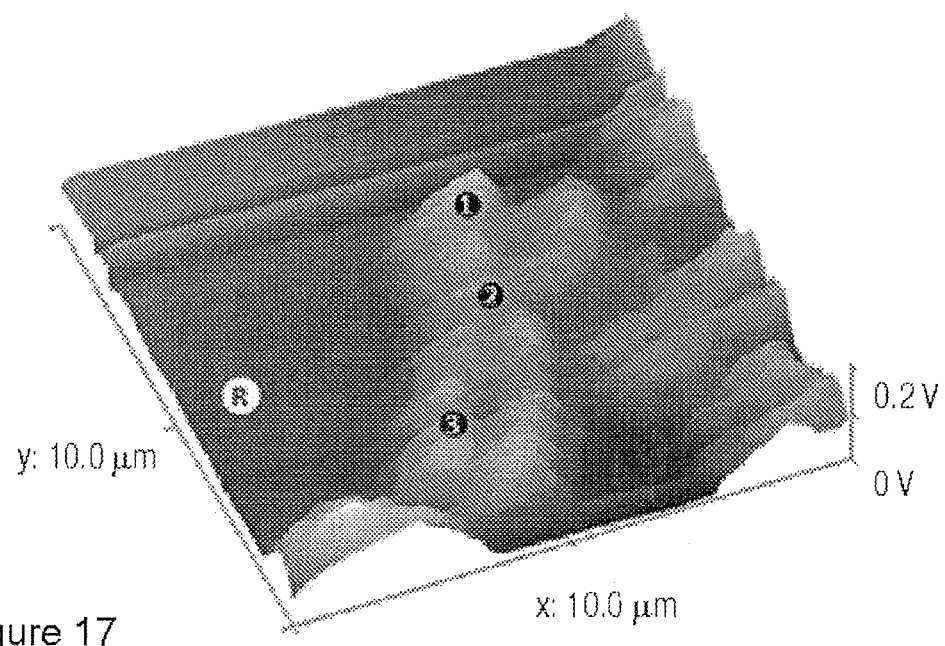
Figure 18:
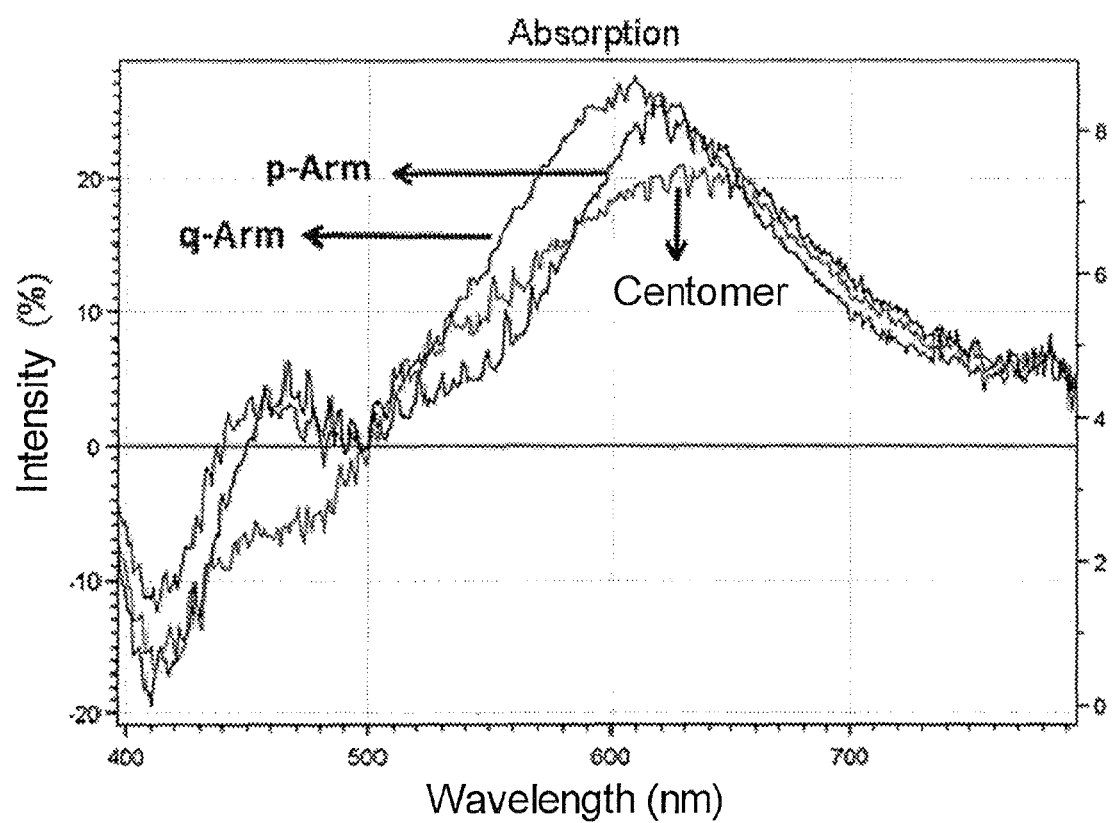

FIG. 17 shows the optical signal from an unstained chromosome in the near field. Measurement points of the near field spectra displayed in FIG. 18: 1=p-arm, 2=centromere region, 3=q-arm FIG. 18 shows the near field spectra in the visible wavelength region of the chromosome in FIG. 17 at points 1, 2 and 3.

DETAILED DESCRIPTION OF THE INVENTION

The present invention relates to a method for analyzing chromosomes by
a) providing a chromosome preparation;
b) measuring at least one interference property of the chromosome preparation; and
c) characterizing at least one chromosome structure by means of the interference property.

The term "chromosome preparation" as used herein comprises any material that contains chromosomes. Chromosome preparations are, therefore, initially preparations merely derived from a test person but which are not further processed. However, chromosome preparations also include processed preparations which, for example, have been modified and optimized for the subsequent measurements by histological or stabilizing methods or by staining techniques. Processing of the chromosomes also comprises placing them on a suitable carrier material such as a microscope slide, which can be pretreated for example with gold, silicon or synthetic materials.

In a preferred embodiment the chromosome preparation according to the invention and containing chromosomes undergoing mitosis is placed upon gold microscope slides or on microscope slides that have been pretreated with gold and treated with the enzyme trypsin. This embodiment provided images which were very rich in contrast.

The term "interference property" as used herein comprises every property and appearance based on interference. Interference describes the overlap of two or more light waves in accordance with the superposition principle. Interference colors and interference patterns are produced for example by applying light onto media of different optical densities, wherein the beam of light is partially reflected and partially transmitted at every phase boundary. The different length of the distances covered by partial light beams lead to optical path differences retardation and, consequently, to relative phase shift. Superposition of the partially reflected partial light beams results in an interference effect. The detection of the interference patterns can be carried out, for example, according to resolved wavelengths.

The term "chromosome structure" as used herein comprises the structural and functional properties of chromosomes as carriers of hereditary information, i.e. the chemical and morphological structures in every stage of the chromosome.

The present invention is based upon spectral, imaging techniques which while dependent upon the wavelength range are able to produce images of both morphological and chemical constituents of a chromosome preparation by means of its interference properties. Without being bound by any special mechanism of action the inventors of the present invention assume that the interference properties of the chromosome preparation arise from the different local geometric layer thicknesses of each chromosome, the different refractive indices of DNA, protein and substrate, and also from the helical structure of DNA in form of cholesteric phases.

If chromosome preparations are observed in diffuse reflection or diffuse transmission, a specific, color band profile results from interference, preferably in the visible light range. In the UV and infrared range, a spatially highly specific local spectral pattern or, a global spectrum characteristic for the respective chromosome can be displayed by interference.

This visualization according to the invention of a banded profile of chromosomes allows a novel classification of chromosomes which exhibits all the advantages of the method according to the invention.

The method according to the invention offers the advantage that there is no need to stain the chromosome preparation but rather that it can be applied to unstained chromosome preparations. In this way the chromosome structure can be characterized independently of variable factors such as the quality of the stain, the degree of condensation and the spreading of the chromosomes. These variable factors which reduce the reliability and significance of measurement data are excluded when analyzing the chromosome structure.

A further advantage of the method according to the invention is that no information about the spectra of the pure components of the chromosomes, i.e. the DNA or protein needs to be available. The spectra of the pure components are calculated from mixed spectra. In this way, conclusions can be drawn about the different concentrations of DNA and protein of the individual chromosomes.

Furthermore, chromosome preparations can be analyzed quickly by the method according to the invention because a time consuming staining of the chromosomes and an equally time consuming analysis of the chromosome banding is superfluous. In addition, the analysis of the interference properties of chromosome preparations can be very well automated and accomplished by computer control. In this way it is possible to realize high though put chromosome screening. Moreover, the method according to the invention is simply to operate and does not require any knowledge of chromosome banding.

The method according to the invention allows displaying morphological and chemical changes such as polymorphism or deletions both quantitatively and qualitatively with a high spectral resolution. By means of the method according to the invention the limitations of classic cytogenic diagnostics are overcome and a refined structure analysis of the chromosomes is possible.

The method according to the invention consequently may be used in pre- and postnatal diagnostics and also in cancer diagnostics because chromosomal variations such as Down's Syndrome or abnormalities of the sex chromosomes are displayed.

The method according to the invention can be carried out before or after prior art techniques for chromosomal analysis such as FISH or SKY in order to, e.g. combine staining techniques and spectral methods. It can also be combined with further spectroscopic and microscopic methods for chromosome analysis such as e.g. atomic force microscopy.

In an advantageous embodiment of the method according to the invention at least one optical property of the chromosome preparation is measured. This measurement can be carried out in addition to the measurement of the interference property.

The term "optical property" as used herein describes all optical and spectral properties and appearances which results from light and from the interaction between light and matter with the exception of interference. The term "light" describes any electromagnetic radiation without limitation to any particular wavelength range. Preferably, the invention is carried out in wavelength rages between a UV/VIS range and a median infrared range. The optical properties comprise both the wave nature and the particle nature of light.

By combining the measurement of interference properties and optical properties a number of measurement variables can be determined which when combined allow more significant statements to be made than those based upon individual measurements. The measurement of a further optical property, such as e.g. absorption provides additional chemical and morphological information about the chromosome structure.

In an advantageous embodiment the interference properties and/or the optical properties of the chromosome preparation are determined by a measurement of spectral properties.

In a further advantageous embodiment the property of the chromosome preparation is selected from the group consisting of interference pattern, intensity dependent upon a wavelength and spectral karyotyping.

The term "interference pattern" as used herein describes both color patterns and shape patterns gray scale from white to black, which are based on interference. They arise from the superposition of waves.

By measuring the distribution of intensity in dependence upon wavelength it is possible to make also statements about the size of the chromosomes.

The term "spectral karyotyping" as used herein describes the production of a karyogram based upon the optical properties of the chromosome preparation and it both categorizes and characterizes the chromosomes. Advantages of the spectral karyotyping are the high resolution as well as the simple and fast manner of execution which allows small chromosomal variations to be determined in both pre- and postnatal cytogenetics as well as in tumor cytogenetics.

In a particularly advantageous embodiment the interference pattern is a global and/or local interference pattern. A local interference pattern is limited to a defined area of a chromosome resulting in a spatially specific interference pattern, e.g. a corrugated pattern. These local interference patterns reflect the banded structure of the chromosome in a very detailed manner which allows conclusions to be drawn about the different layer thicknesses in the chromosome. A global interference pattern is an interference pattern of a complete chromosome wherein the measuring orifice is adjusted such that it captures the complete chromosome and a total spectrum of the chromosome is measured. By means of the position of the total spectrum, such as e.g. of the maximum and the two flanks, the chromosomes can be identified as groups and their morphology, such as e.g. the position of the centromere region, can be described as metacentric, submetacentric or telocentric.

In a further embodiment the interference property and/or the optical property of the chromosome preparation is measured in a mode selected from the group consisting of transmission mode, reflection mode, polarization mode, absorption mode, excitation mode and emission mode.

The term "transmission mode" describes a mode in which light is analyzed, after passing through the matter in a directed or diffuse manner, in particular, at an angle between 0° and 90°. Thus, the term "transmission mode" comprises both the angle dependent diffuse as well as the directional transmission mode. The term "reflection mode" describes a mode in which light is analyzed which has been reflected from material in either a directional manner or a diffuse manner and, in particular, at an angle between 90° and 180°. The term "diffuse reflection" describes reflection at a large roughness in relation to the wavelength which results in scattering. The term "directional reflection" describes the reflection reflecting the light at the surface with the incident angle=the emergent angle. The term "polarization mode" describes a mode in which the waves are directed in a relatively uniform direction. The term "absorption mode" describes a mode in which the amount or the presence of light absorption is measured. The term "excitation mode" describes a mode in which an excitation of e.g. a fluorophore occurs and is detected. The term "emission mode" describes a mode in which the amount or the presence of an emission of light is determined. Each mode is spectrally resolved at different wavelengths.

In addition, different recording modes can be used to measure interference properties and/or the optical properties of the chromosome preparation. Examples of spectral imaging methods are whiskbroom mapping, staring as a 2D wavelength scan and pushbroom as a line scan with spectral splitting, computertomographic imaging spectrometry and confocal microscopy. Other possibilities for the measurement of interference include ellipsometry, optical coherence tomography, speckle interferometry, white light interferometry, reflection anisotropy spectroscopy, angle dependent measurements and all other methods for measuring interference.

In whiskbroom mapping, image areas are scanned in a point wise manner, i.e. selectively illuminated and detected. In this way no surrounding areas contribute to the absorption so that even small differences in absorption can be visualized. An advantage of this embodiment according to the invention is the high degree of spectral resolution.

In the case of the staring method complete two dimensional images are recorded with the wavelength being changed between the recordings. The selection of wavelengths can be made in different ways. For both the staring method and the method according to the invention in general, special filter wheels, linear variable filters such as electrical variable filters or imaging interferometers if Fourier transformations need to be employed, are suitable.

In the case of the pushbroom method the object is recorded through a slot in a "prism-grating-prism" optical arrangement. In this way the light is splitted in the second axis, i.e. the wavelength and recorded on the camera. In order to integrate the second spatial coordinate the object must be moved. This arrangement is specially suitable for online and inline analyzes.

In a particularly preferred embodiment the diffuse reflection mode is used which is particularly suitable for measurement of the spectral properties and interference properties of chromosome preparations. In this mode, the chromosome structure is very specifically displayed as a banded profile.

In a further embodiment at least one parameter of the property of the chromosome preparation is determined.

The term "parameters" describes variables which are determined by at least one calculation step such as the formation of the first derivative from the measured interference and optical properties of chromosome preparations. The parameters thereby provide additional information about the chromosome structure.

In an advantageous embodiment the parameters are selected from the group consisting of transmission coefficient, reflection coefficient, absorption coefficient and scattering coefficient.

The term "transmission coefficient" as used herein is a measure for the reduction of the light which passes through the medium and/or the chromosome preparation, i.e. the obstructing body. It is defined as the ratio of the intensity of light passing through an object to the intensity of the incident light. It represents the difference of the original amount of light minus absorption, scattering and reflection.

The term "reflection coefficient" as used herein is a measure of the reflected intensity, i.e. of the ratio between reflected and of incident radiant flux. It can be calculated with the help of the Fresnel formulae.

The term "absorption coefficient" as used herein and also known as "absorption constant" is a measure of the strength of absorption. In optics it represents the imaginary portion of the complex refraction index.

The term "scattering coefficient" as used herein is a measure of the scattered intensity. The scattering coefficient describes that portion of light which is scattered within a partially transparent medium, such as a cloud of particles not subject to absorption per distance unit.

In addition to the coefficients it is possible to calculate a transmission factor, a reflection factor, an absorption factor, a polarisation factor and a scatter factor as anisotropic parameters.

In a particularly advantageous embodiment the property and/or parameter of the chromosome preparation are analyzed by means of at least one multivariate technique.

The term "multivariate technique" describes a technique which does not analyze one variable alone but rather analyzes the combined effect of several variables simultaneously and their dependence structure. Multivariate techniques can be divided into structure probing methods such as variance analysis or structure equation models and structure identifying methods such as neuronal nets, factor analysis and principal component analysis.

By means of the method according to the invention with at least one multivariate technique large quantities of data can be produced in a short time, for example, several megabytes per millisecond with overlying information about, for example, absorption and scattering. To that extent, the compression of the data to essential items of information as well as the exclusion of superfluous information plays an important role. This can be attained by multivariate techniques allowing a compression of information or also a reduction of the original data.

In this way the relevant information is extracted from a large number of measured values and variables.

One objective of, for example, the analysis of principal components is to closely approach a multitude of measure values and spectra by a smaller number of as significant as possible linear combinations, the principal components. In the principal component analysis, measured values or spectra are combined in a manner corresponding to a maximal variance, since the variance is a measure of the information content. In the principal component analysis the data exists as a point cloud in an n-dimensional co-ordinate system as a point cloud. A new co-ordinate system is placed within this point cloud and rotated. A first axis is positioned within the point cloud such that the variance of the data in the direction of this axis is maximal. A second axis stands vertically upon the first axis. In its direction the variance is the second largest. In the case of n-dimensional data there are, in principle, n axes which are positioned orthogonally to one another. The total variance of the data is the sum of these "axis variances". These axes are represented by factors which represent the relevant information content of the data. Frequently the contents of the factors cannot be interpreted unambiguously.

A classification of the chromosomes is obtained from the principal component analysis of the properties and/or parameters of the chromosome preparation. The different principal components provide information and background data as to why certain chromosomes belong to a particular class. The principal components provide information about parameters which are not directly measurable, such as, e.g. size, shape, position of the centromere region, banding, DNA and/or protein content. This information can be used to make statements about variabilities, of e.g. heterochromatic regions of individual chromosomes. The models of the multivariate data analysis can then be used to predict unknown chromosomes with aberrations. Depending upon the model, the classification entitlement or one or more values for the target dimensions, for which the model was designed, are obtained.

In addition, by means of the combination of the method according to the invention with a multivariate technique it is possible to make statements which cannot be derived from methods of the prior art. With the help of multivariate resolution of curves it is possible to separate e.g. mixed spectra into basic spectra. Consequently, the spectra of the pure constituents of the chromosomes, namely DNA and protein, can be calculated from the mixed spectrum of a mixed preparation such as the chromosome preparation. In turn, this allows statements about the different concentrations of DNA and protein in the individual chromosomes to be made.

Furthermore, by means of the multivariate technique a new classification model for the chromosomes of humans or other species can be developed without the need for staining. To that end, the properties and parameters of the chromosome preparation such as the absorption and/or reflection properties of the DNA and protein fractions in the UV range, the DNA orientation or the layer thicknesses in the VIS range are incorporated into the multivariant analysis and serve to provide a quick, reliable and automatable karyotyping and classification. This classification has been verified by methods of the prior art.

In a particularly advantageous embodiment the multivariate technique is a principal component analysis or a pattern recognition method.

The principal component analysis is a multivariate statistical method which serves to structure and display extensive sets of data by approximating a majority of statistic variables by a smaller number of as significant as possible linear combinations, the "principal components".

In pattern recognition methods, measured signals are automatically arranged in categories.

The central point therein is the recognition of patterns, i.e. the characteristics, which are common to one category and which separate them from the content of other categories.

Multi-path methods such as the N-Way multivariate analysis of data, the parallel factor analysis or the multivariate resolution of curves are particularly suitable for the analysis of chromosome preparations because the data are highly dimensional. In particular, the multivariate resolution of curves permits the compression of data in n-dimensional space. The integration of side conditions, such as e.g. positive spectra and the integration of previous knowledge, allows very quick calibration free models to be produced and, moreover, the latent variables of these can be easily interpreted.

The chromosome structure can be a chemical and/or a morphological chromosome structure. The term "chemical chromosome structure" describes the molecular structure of the chromosomes such as the concentrations of DNA and protein or the arrangement of macromolecules and deletions. The term "morphological chromosome structure" describes the microscopic and macroscopic structure and conformation of the chromosomes such as chromosome size, chromosome thickness, chromosome aberrations, chromosome topology, banded profiles and layer thicknesses.

In an advantageous embodiment the properties of the chromosome preparation are measured in a spectral range of approximately 180 nm to approximately 25,000 nm. The UV range of approximately 180 nm to approximately 400 nm is particularly suitable for analyzing the chemical structure of the chromosomes and for the separate display of the spectra of the DNA and protein. The VIS range of between approximately 400 nm and approximately 700 nm is particularly suitable for illustrating the banding of the chromosomes thus, the morphological chromosome structures. Furthermore, measurements in the VIS range are extremely inexpensive embodiments. The near infrared range of approximately 700 nm to approximately 3,000 nm and the median infrared region of approximately 3,000 to approximately 25,000 nm are particularly suitable for analyzing of the chemical chromosome structure.

In one embodiment the interference properties of the chromosome preparation are measured by means of a near field microscope. In a preferred embodiment a solid immersion lens attached to the microscope is used. In this way, the interference properties and the optical properties of the chromosomes are measured with high lateral resolution.

This resolution can be considerably below 30 nm with the result that, for example, chromatid properties as well as microdeletions or translocations can be detected. Preferably the resolution lies in the range of ≤30 nm, more preferred of approximately 20-30 nm, most preferred of approximately 25 nm.

The term "near field microscope" as used herein describes a microscope which can be used in the near field (WO 98/58288). The near field is the range which lies below the diffraction limit of the microscope. It is characteristic of the near field that only a part of the electromagnetic energy present is propagated away from the source, as in the case of the far field, while the remainder fluctuates around the source or the antenna. This localised electromagnetic field, also described as an evanescent field, is used in near field microscopy with the means of detection being located within the near field.

In a preferred embodiment a solid immersion lens is used with the microscope. The solid immersion lens optimizes the optical throughput and, thereby, the optical spectroscopy in the near field. The use of the solid immersion lens in the near field allows a multi dimensional fluorescence spectroscopy which is advantageous in the single molecule detection. With the help of multi dimensional fluorescence spectroscopy, compounds can be separated spectroscopically or non-destructively if the different emission spectra are recorded with different excitation frequencies. In that way, a 3D image of the different spectra is produced wherein the excitation maxima and the emission maxima of individual molecules can be clearly distinguished.

The advantage of this method according to the invention lies in the high lateral resolution which allows micro deletions or translocations of unstained chromosomes to be identified more precisely.

With the method according to the invention the interference properties of the chromosome preparation can be measured in the reflection near field mode which generates a positive image of the chromosomes. The interference properties of the chromosome preparation can also be measured in the photon tunnel near field mode wherein a negative image of the chromosomes is generated.

The term "reflection near field mode" describes a mode in which the interaction of the evanescent field localised on the sample is detected with the solid immersion lens. The radiation free field can couple into a dielectric medium and then further propagate in the lens. The reflected near field is detected in the far field by a measuring field aperture and produces a positive image. The term "photon tunnel near field mode" describes a mode in which the focal plane of the lens is adjusted such that the light impinges at the tip at the angle of total reflection. Thereby the evanescent field around the solid immersion lens is established. By approximating the field to the sample, photons tunnel into the sample and lead to a loss of reflected light in the lens. The reduction of intensity can be detected directly in the far field. Such imaging produces a negative image (Merz and Kessler, 2007).

In a further embodiment, measurements are made in the near field by the method according to the invention wherein spectroscopic methods comprising UV-VIS-NIR-IR, fluorescence (Caspersson et al. 1968) or Raman but not limited thereto are incorporated. In this way, characteristic, chemical and morphological parameters of each chromosome are detected.

In a further embodiment the method according to the invention can be carried out in the near field and combined with spectroscopy and the FISH technique in the far field. This results in combining fast screening opportunities and highly resolving measurements.

In a particularly preferred embodiment the spectral properties of the chromosomes are measured in the near field. As a result of the evanescent fields, the near field spectra possess a different content of information with respect to the far field spectra and are not directly comparable with the known far field spectra. In the far field spectrum the information is measured as the sum of the superimposed interferences. The difference in the near field spectra thereby results from the lateral locally resolved measurement point.

In an embodiment the method according to the invention is combined with a scanning force technique, preferably selected from the group consisting of scanning probe microscopy, atomic force microscopy, scanning near field microscopy, optical scanning near field spectroscopy and near field spectroscopy (Oberringer et al. 2003).

In a particularly preferred embodiment a near field microscope with a solid immersion lens is used for the analysis of unstained chromosomes.

DESCRIPTION OF THE EMBODIMENTS

In each of the FIGS. 1A to D an unstained chromosome set on different materials and measured by different methods is shown:
A: Preparation on glass, reflected light dark field (Reflection arrangement 45/0)
B: Preparation on a Si-wafer, reflected light dark field (Reflection arrangement 45/0)
C: Preparation on gold, reflected light dark field (Reflection arrangement 45/0)
D: Preparation on gold, reflected light bright field (Reflection arrangement 0/0)

A striking feature of all dark field images is the specific color profile present for each chromosome. This can be attributed to different layer thicknesses, refraction indices and orientations of the chromosomal DNA.

1. Representation of Chromosomes by Whiskbroom Mapping

In one embodiment of the method according to the invention the whole chromosome set was measured point wise by whiskbroom mapping. This involved recording a complete spectrum in the preferred wavelength region from every point in the X and Y-directions. Preferably only a single detector was used, such as, for example, a photomultiplier or a diode array detector. The development of the image occurred sequentially by combining many measurement points. In addition to a high spectral resolution it was possible to carry out a detailed analytical point resolved characterization up to the diffraction limit.

1.1 Giemsa Stained Chromosomes

In FIG. 2 a UV-VIS Near Infrared (NIR) spectrum of the GTG banded chromosome No. 2 is shown. The marked region in FIG. 2A illustrates the section of the used measuring field aperture and measures about 0.5 µm in the image plane. The aperture was positioned such that it included a dark G-band. FIG. 2B shows an absorption spectrum for wavelengths in the UV/VIS range and the NIR range of the chromosome section marked in FIG. 2A. FIG. 2C shows the spectral distribution at 550 nm in absorption with each individual pixel recorded with a geometric resolution of 250 nm and a spectral resolution of 1 nm. The dark pixel areas reflect areas with high absorption of the Giemsa stain and thereby correspond to the schematic banded profile for chromosome No. 2.

An advantage of the embodiment according to the invention in contrast to imaging methods of the prior art lies in the point illumination and detection of each pixel. Since no surrounding areas contribute to absorption, small absorption differences can also be rendered visible. A further advantage of this embodiment according to the invention is the high spectral resolution which however requires a lot of time to describe the whole chromosome set. This is shown particularly clearly in FIG. 2D by a comparison made with an ideogram where each band can be assigned directly. By this, spectral distribution images, which are characteristic for each chromosome, can be produced for each wavelength, even in the near infrared.

1.2 Representation of Unstained Chromosomes by VIS Measurement in Reflection

When measuring unstained chromosomes a reflection spectrum was recorded for each chromosome. When doing so, the measuring field aperture was adjusted such that only one chromosome was captured during each measurement procedure. Consequently 46 individual spectra were obtained from 46 chromosomes. Since the background for dark field measurements is black the measuring field aperture could be varied after a one-time comparison, for example, with barium sulphate as a diffuse scattering agent without an increasing background noise.

As a result of the measurement arrangement and geometry, different red-yellow-green color profiles were obtained for each chromosome. When applying trypsin, a reduction of the red color contents is observed over the time, which leads to the formation of color structures and specific profiles resembling a banding of the chromosomes. If the exposure time is too long this causes deformation of the chromosomes. At the beginning of the trial series no specific band structure existed. The reason for this are non-specific protein sheaths which cover the real structure. With increasing trypsinization the band structure became more distinct and the non-specific protein sheathing diminished.

Chromosome No. 2 which can be seen in FIG. 3B has been measured at 5 different points with an aperture diameter of 0.5 µm. For the respective region a specific reflection spectrum (FIG. 3A) can be seen which is based upon the interferences arising from the different layer thicknesses. A comparison was done with barium sulphate.

Contrary to this, the reflection spectrum of the entire chromosome No. 2 can be seen in FIG. 4. For this, the measurement field aperture was adjusted such that the complete chromosome was captured during each measurement procedure. In that context it is to be seen that the individual interferences are lost within the total spectrum and transfer to a global spectrum. Furthermore, with increasing time of trypsinization there is a reduction in intensity and a change of maximum and flank conditions.

FIG. 5 displays the peak maximum displacement over the time of trypsinization. This revealed that the peak maximum varied with time pointing to a reduction of the layer thickness. After about 100 s a state of equilibrium was reached, which was not altered upon further trypsinization thereby marking the endpoint of the trypsinization. Beyond that point there only followed the deformation of the chromosomes.

After a suitable time of trypsinization of about 100 s, which depends upon the activity of the enzyme, a reflection spectrum was recorded for each chromosome. Here, as an example, the range between 400 and 800 nm was selected. Thereby the measurement aperture was adjusted such that only one chromosome was processed during each measurement procedure. The comparison was done with barium sulphate.

From FIG. 6A it can be seen that the diploid chromosome pair No. 1 exhibits the highest and the diploid pair No. 22 the lowest level of reflection. In order to ensure in the following model that the intensity and, therefore, the size is not the dominant factor in the data, the first derivative was calculated thereby emphasizing the maximum at the null point and the flanks (FIG. 6B). By this means it is clear that one characteristic riffle pattern exists per each spectrum, which is attributable to the banded structure of the respective chromosome. In combination with the multivariate data analysis which extracts a few latent factors out of the pretreated spectra a classification model for the chromosome pairs can be developed.

Figure 7A:
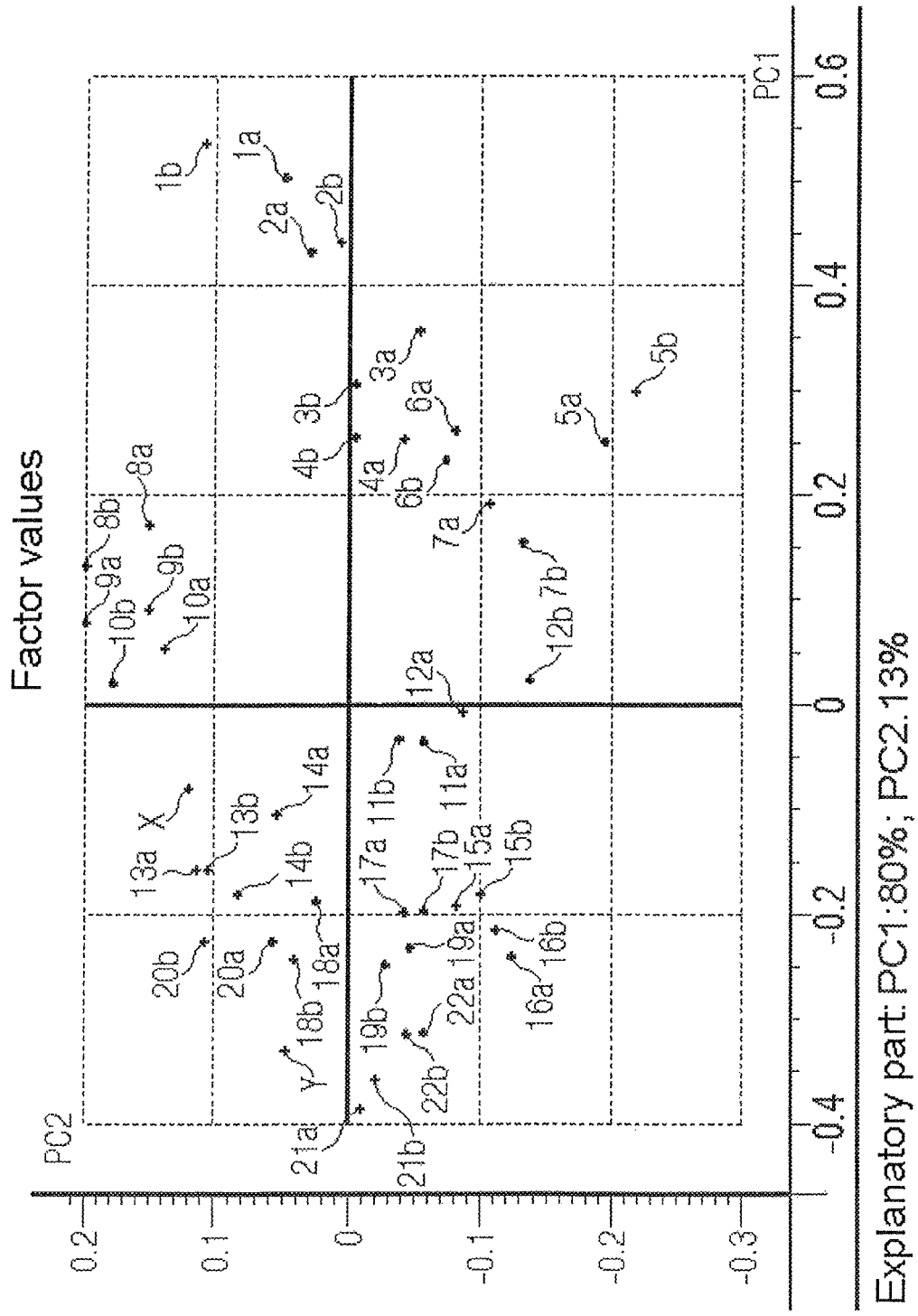
Figure 7B:
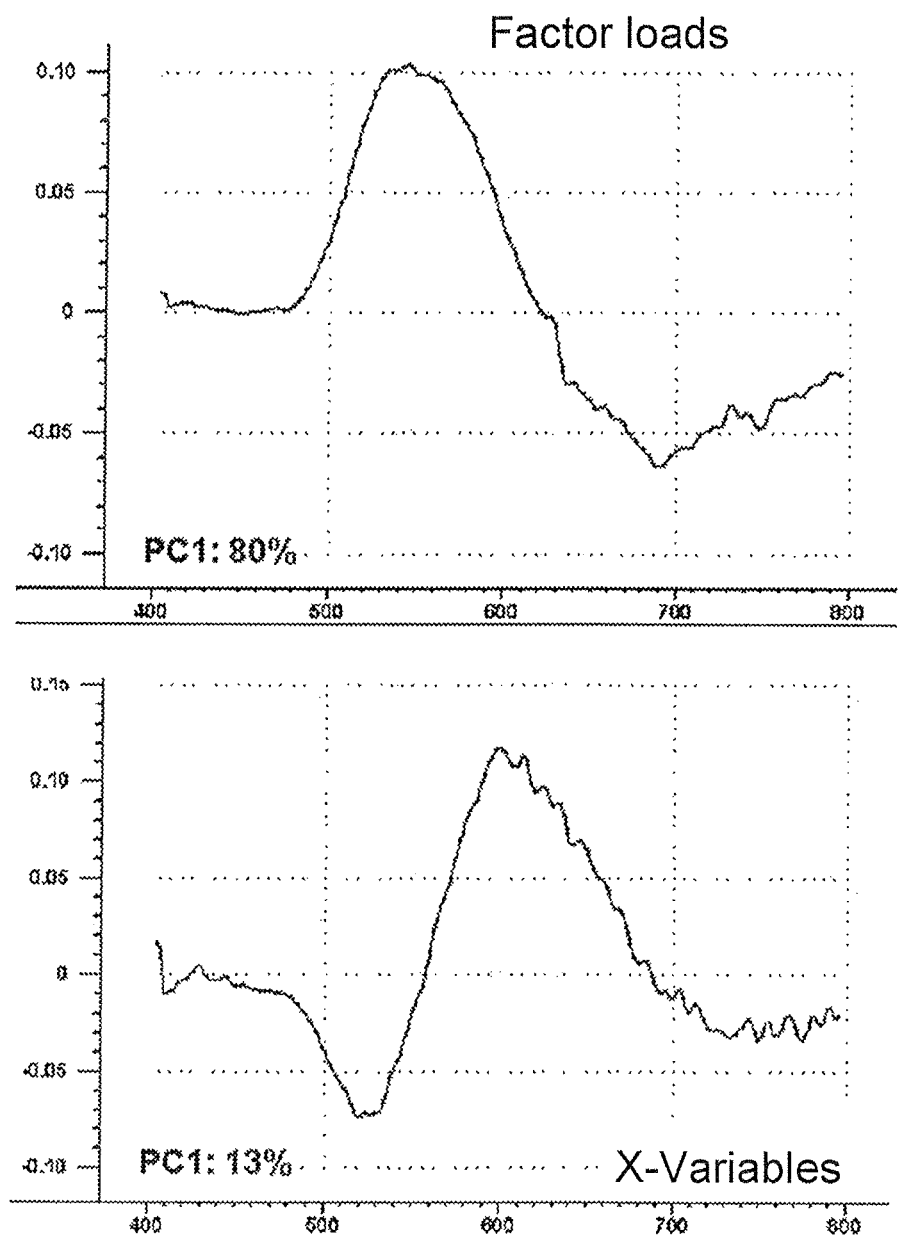

The model of a principal component analysis in FIGS. 7A and 7B shows all 46 chromosomes separated in pairs. The verification of the chromosome numbers was confirmed by MFISH.

1.3 Representation of Unstained Chromosomes by UV Measurements in Reflection

To carry out UV measurements in the reflection mode, a reflection spectrum (bright field-reflected light) in the range of 240 nm to 400 nm was recorded. After calibration with a gold blank position the measurement field aperture has to be kept constant. If, due to chromosome size, the measurement field aperture is varied, a new calibration must occur. Furthermore, only one chromosome was captured per measurement procedure (FIG. 8).

Figure 9B:
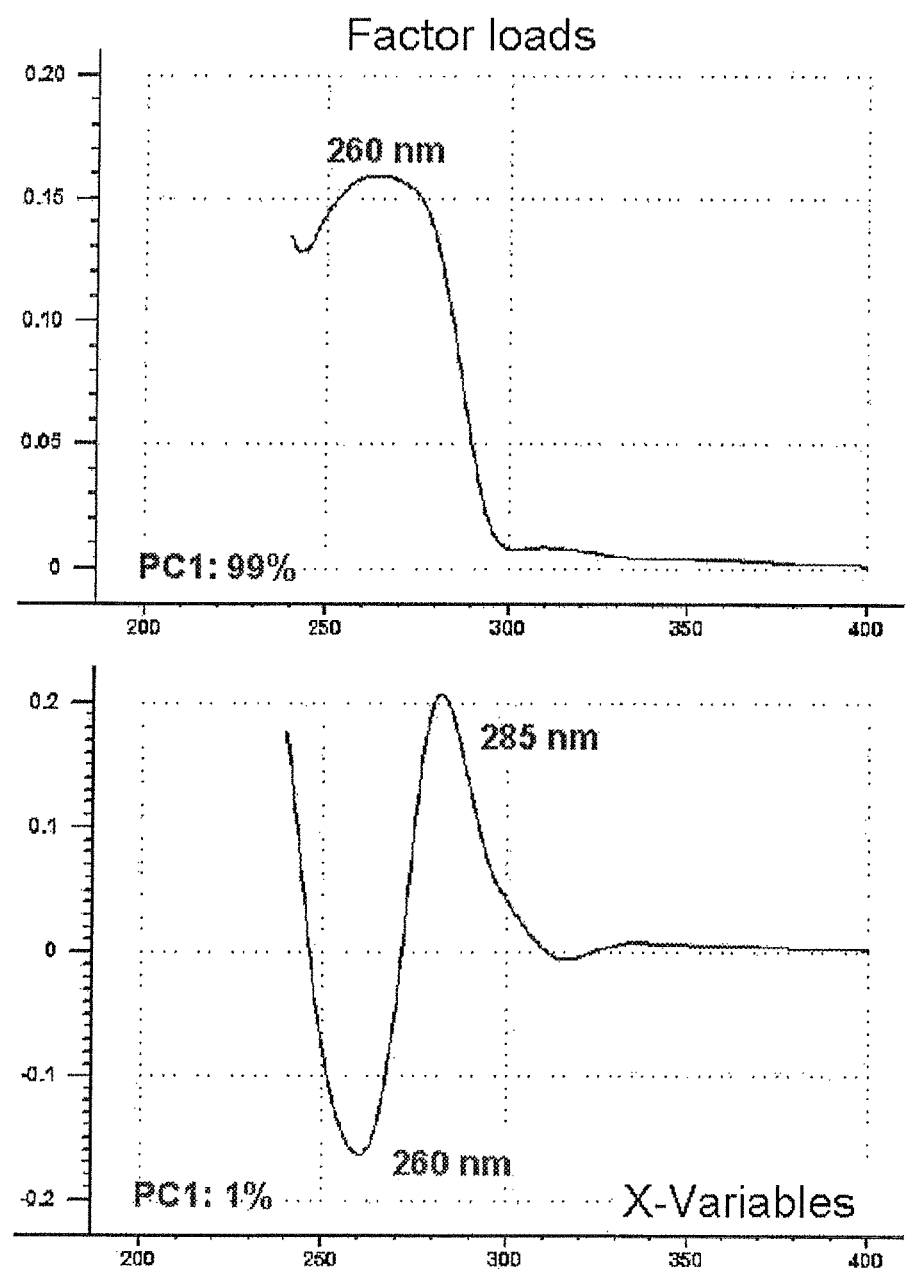

With the subsequent principal component analysis—as for the dark field measurements—it was possible to develop a classification model for the UV range (FIGS. 9A and 9B). The first principal component and thereby the largest variance in the spectra can be described by an associated factor diagram. This shows the total absorption at 260 nm. In order to even distinguish the chromosome pairs 14, 15 and 16 the second principal component was included. This shows the spectral sequence of the factor diagram, which exhibits 260 nm in the negative range and 285 nm in the positive range. Since chromosomes are not of pure DNA, but each chromosome is specifically associated with different protein islands, the range of about 285 nm could be assigned to the protein fraction. A subsequent multivariate curve resolution splitted these mixed spectra into basic spectra. An advantage of the method according to the invention is that there is no need for information about the spectra of the pure components to be available. The spectra of the pure components were calculated from the mixed spectrum. In this way, two spectra were obtained, corresponding to a pure DNA fraction and a pure protein fraction. In this way statements can also be made about the different DNA and protein concentrations of the individual chromosomes (FIGS. 10A and 10B).

A set of human chromosomes was illuminated monochromatically at 260 nm to correspond with the DNA and at 285 nm to correspond with the protein fraction. The associated absorption values were registered in reflection for each pixel area such that two sets of data could be generated from them. When integrating the absorption values, the chromosomes were displayed and identified.

2. Representation of Chromosomes by 2D-Wavelength Scanning 2.1 Unstained Chromosomes In the representation of chromosomes by means of 2D-wavelength scanning the unstained set of chromosomes is planar illuminated and the image is evaluated in a reflection mode or also a transmission mode (FIG. 11). Thereby, the spatial information is simultaneously and the spectral information sequentially recorded, resulting in a stack of images (FIG. 11B). A spectrum, which is characteristic for each chromosome, can be generated along the wavelength for each pixel region of the stack of images. Furthermore, a multivariate image analysis in the form of a principal component analysis can follow. Using chromosome No. 5 as an example it is shown that different contents of information are present for each principal component (PC) which can be used for targeted distinguishing between the chromosomes (FIGS. 11 A, C, D). An advantage of this method is the simultaneous recording of the total chromosome set as well as the targeted selection of the information carrying wavelengths.

3. Representation of Chromosomes by Line Scanning 3.1 Giemsa-Stained Chromosomes In comparison with the whiskbroom mapping method, the total spectral information and, thereby, the banded profile was captured in a single step with the help of line scanning, also known as pushbroom method (FIG. 12). The maximal image section for the entry slot, when enlarged 1000 times, amounted to 50×0.5 µm in a lateral direction as well as to 5 nm for the spectral resolution. The area of the chromosome marked with a frame schematically depicts the entry slot in the image plane and amounts to 10×0.5 µm. When giving consideration to the Nyquist limit and the resulting diffraction limit the best possible lateral resolution—starting from 78 nm per pixel—was 128 pixels for a chromosome 10 µm long. In this way it was possible to determine a specific absorption spectrum for every point along the X-axis which could then be assigned to the banded profile.

3.2 Unstained Chromosomes

A further possibility of identification and characterisation is represented by the pushbroom method in incident light dark field. Here, too, as described above, the total spectral information per chromosome can be obtained in one step. The area marked with a frame schematically represents the entry slot in the image plane and generates a spectral image along the local axis. It is possible for the associated spectrum to be extracted from each point of the local axis (FIG. 13).

4. Measurements of the Optical Properties of Chromosomes Using a Near Field Microscope In an embodiment according to the invention the optical properties of a chromosome were measured in the near field. To that end a near field microscope with a solid immersion lens and a microspectral photometer were used.

4.1 Assembly of the Measurement Apparatus from a Near Field Microscope and a Spectral Photometer A universal microscope, a near field microscope with a solid immersion lens and a spectral photometer were assembled together such that it was possible to carry out microscopic and spectroscopic examinations under reflected light and transmitted light. Furthermore, illuminations, mono chromatic illuminators to select wavelengths for excitation and emission, detectors and iris type pinholes to adjust the Koehler illumination were put in place around the microscope and the spectrometer. The arrangement is shown schematically in FIG. 15.

4.2 Representation of Chromosomes by Near Field Microscopy

The chromosomes in question were prepared, preferably on gold microscope slides, and then exposed to treatment with trypsin. The preparations were scanned, point by point, with a solid immersion lens. The method is based upon the interaction between an optical field and the structure of the chromosome. As the different structures are packed at different density levels, the intensity of the interaction within the sample varies, this was registered by a photo detector. FIG. 16 displays an intensity profile produced in this way and extending over the length of a chromosome. The chromosomes could be represented by means of reflection near field microscopy, photon tunnel near field microscopy and/or fluorescence near field microscopy.

4.3 Representation of Chromosomes by Near Field Spectroscopy

In order to record highly resolved spectra of local chromosome structures it was focused on selected points of individual chromosomes. FIG. 17 shows a chromosome displayed enlarged by near field spectroscopy. As a reference (R) for the spectroscopy, an empty gold space in the preparation was recorded as a reference spectrum. Subsequently, VIS-spectra were recorded at three characteristic places on the chromosome. The measurement, which is represented in FIG. 18, was made on the p-arm (1), on the centromere region (2) and on the q-arm (3) within a wavelength range of 400 to 800 nm. Furthermore, it could be shown that the supposed noise which appeared was not a signal noise but rather caused by the structure of the chromosome. The characteristic bands are attributable to the varying chromatid packing and, thereby to different refraction indices.

EXAMPLES

1. Preparation of the Metaphase Chromosomes

Blood lymphocytes taken from men and women whose karyotype had previously been shown to be normal 46, XX or XY were used for the manufacture of chromosome preparations. The sample of the blood culture, as well as the preparation of the blood culture, was carried out in accordance with the standardized methods and protocols of human cytogenetics.

2. Sample of Blood Culture

Venous blood was transferred to a small sterile tube wetted with heparin. The full blood was transferred under sterile conditions into culture flasks and mixed with chromosome medium B (Biochrom AG, Catalogue No. F5023). The T-lymphocytes were stimulated during a cultivation time of 72 hours at 37° C. in an incubator to undergo cell division.

3. Processing of the Blood Culture

Colcemid was added to the blood culture, incubated at 37° C. for 30 minutes and then centrifuged for 6-7 minutes. The supernatant was removed by suction down to the lower cone. The sediment was then shaken and heated KCl was added with constant shaking. The small tubes were sealed with Parafilm™, incubated in a water bath for 20 minutes at 37° C. and then centrifuged for 6-7 minutes. The supernatant was removed by suction down to the lower cone, the sediment was shaken and then 5 ml of Fixans (methanol and acetic acid) were added. The fixed sediment was incubated for 30 minutes in a refrigerator and centrifuged for 6-7 minutes, after which the supernatant was removed by suction down to the lower cone. The resulting chromosome preparation was then diluted with Fixans, the chromosomes were transferred to microscope slides previously treated with Fixans and "aged" for 60 minutes on a heating plate at 100° C.

4. Microscope Slide

Highly different materials can be selected as microscope slides for the present invention—such as, e.g. glass, plastic, Si-wafer or gold microscope slides. Reflection measurements with microscope slides such as gold microscope slides (Erie Scientific: Biogold) and Si-wafers resulted in images very rich in contrast.

Finally, it is to be noted that despite the formal reference back to one or more specific claims all features which are named in the application documents and in particularly in the dependent claims are also to be independently protected either individually or in any preferred combination.

References

Bayani J M, Squire J A
Applications of SKY in cancer cytogenetics,
Cancer Invest. 2002; 20(3):373-86.
Caspersson T., Farber S., Foley G. E., Kudynows J., Modest E. J., Simonsson E., Wagh U., and Zech L.
Chemical Differentiation Along Metaphase Chromosomes,
Experimental Cell Research 49, 219-& (1968).
Merz T. and R. W. Kessler
Spectroscopic Imaging in the Near Field with an Apertureless Solid Immersion Lens System
Proceedings of SPIE 6631, (2007).
Oberringer M., Englisch A., Heinz B., Gao H., Martin T., and Hartmann U
Atomic force microscopy and scanning near field optical microscopy studies on the characterization of human metaphase chromosomes
European Biophysics Journal with Biophysics Letters 32, 620 (2003).
Zhao L, Hayes K, Glassman A,
A simple efficient method of sequential G-banding and fluorescence in situ hybridization,
Cancer Genet Cytogenet. 1998 May; 103(1):62-4.
WO 98/58288

The invention claimed is:

1. A method for analyzing chromosomes by
a) providing an unstained chromosome preparation;
b) measuring at least one interference property of the unstained chromosome preparation; and
c) characterizing at least one chromosome structure by means of the interference property,
wherein the interference property of the chromosome preparation is an interference pattern.

2. The method according to claim 1, wherein in addition at least one optical property of the chromosome preparation is measured.

3. The method according to claim 2, wherein the optical property of the chromosome preparation is selected from the group consisting of intensity dependent upon a wavelength and spectral karyotypization.

4. The method according to claim 1, wherein the interference pattern is a global and/or a local interference pattern.

5. The method according to claim 1 or 2, wherein the interference and/or optical property of the chromosome preparation is measured in a mode which is selected from the group consisting of transmission mode, reflection mode, polarization mode, absorption mode, excitation mode and emission mode.

6. The method according to claim 1 or 2, wherein at least one parameter of the interference and/or optical property of the chromosome preparation is determined.

7. The method according to claim 6, wherein the parameter is selected from the group consisting of transmission coefficient, reflection coefficient, absorption coefficient and scattering coefficient.

8. The method according to claim 6, wherein the interference and/or optical property and/or the parameter of the chromosome preparation is analyzed by means of at least one multivariate technique.

9. The method according to claim 8, wherein the multivariate technique is a principal component analysis or a pattern recognition method.

10. The method according to claim 1, wherein the chromosome structure is a chemical and/or a morphological chromosome structure.

11. The method according to claim 1, wherein measurement of the interference property is made in a spectral range of approximately 180 nm to approximately 25,000 nm.

12. The method according to claim 1, wherein the interference property of the chromosome preparation is measured using a near field microscope.

13. The method according to claim 12, wherein a solid immersion lens is used on the microscope.

14. The method according to claim 12, wherein the interference property of the chromosome preparation is measured in the photon tunnel near field mode.

15. The method according to claim 12, wherein the method is combined with a scanning force technique, preferably selected from the group consisting of scanning probe microscopy, atomic force microscopy, scanning near field microscopy, optical scanning near field microscopy and near field spectroscopy.

* * * * *